United States Patent
Okubo et al.

(10) Patent No.: US 9,164,021 B2
(45) Date of Patent: *Oct. 20, 2015

(54) REAGENT PREPARING DEVICE, SPECIMEN PROCESSING SYSTEM AND REAGENT PREPARING METHOD

(75) Inventors: Koichi Okubo, Kobe (JP); Noriyuki Nakanishi, Kakogawa (JP); Masahiko Oguro, Kobe (JP); Tomoyuki Asahara, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 650 days.

This patent is subject to a terminal disclaimer.

(21) Appl. No.: 12/711,676

(22) Filed: Feb. 24, 2010

(65) Prior Publication Data

US 2010/0216224 A1    Aug. 26, 2010

(30) Foreign Application Priority Data

Feb. 26, 2009 (JP) ................................ 2009-044099
Mar. 30, 2009 (JP) ................................ 2009-082685

(51) Int. Cl.
| G01N 21/00 | (2006.01) |
| G01N 15/14 | (2006.01) |
| G01N 1/38 | (2006.01) |
| G01N 35/10 | (2006.01) |
| G01N 35/00 | (2006.01) |

(52) U.S. Cl.
CPC .................. *G01N 15/14* (2013.01); *G01N 1/38* (2013.01); *G01N 35/1002* (2013.01); *G01N 2035/00534* (2013.01)

(58) Field of Classification Search
CPC ................................ G01N 15/14; G01N 21/00
See application file for complete search history.

(56) References Cited

U.S. PATENT DOCUMENTS

| 5,800,056 A | 9/1998 | Suzuki et al. |
| 6,457,852 B1 | 10/2002 | Hiraoka et al. |
| 2002/0175183 A1 | 11/2002 | Schell et al. |
| 2002/0186613 A1 | 12/2002 | Hiraoka et al. |
| 2005/0142883 A1 | 6/2005 | Hiraoka et al. |
| 2007/0141845 A1 | 6/2007 | Hiraoka et al. |
| 2007/0212261 A1* | 9/2007 | Tanaka et al. ................... 422/67 |
| 2010/0055772 A1* | 3/2010 | Nagai et al. ................ 435/287.3 |
| 2011/0045498 A1* | 2/2011 | Lindberg et al. ............. 435/7.21 |

FOREIGN PATENT DOCUMENTS

| JP | 59-171830 A | | 9/1984 |
| JP | 10-232156 A | | 9/1998 |
| JP | 11-126764 A | | 5/1999 |
| JP | 2000-126767 | * | 5/2000 |
| WO | WO 2009-031461 A1 | | 3/2009 |
| WO | WO2009026919 | * | 3/2009 |

* cited by examiner

*Primary Examiner* — Jyoti Nagpaul
(74) *Attorney, Agent, or Firm* — Brinks Gilson & Lione

(57) ABSTRACT

A reagent preparing device capable of supplying a mixed solution, including a first liquid and a second liquid, to a measurement section for measuring a specimen using the mixed solution as a reagent, the reagent preparing device comprising: a first mixed solution container for accommodating the mixed solution; a second mixed solution container for accommodating the mixed solution; and a controller for controlling supply of the first liquid and the second liquid to supply the first liquid and the second liquid to the first mixed solution container, and to supply the first liquid and the second liquid to the second mixed solution container, is disclosed. A specimen processing system, and a reagent preparing method are also disclosed.

21 Claims, 22 Drawing Sheets

REAGENT PREPARING DEVICE, SPECIMEN PROCESSING SYSTEM AND REAGENT PREPARING METHOD

RELATED APPLICATIONS

This application claims priority under 35 U.S.C. §119 to Japanese Patent Application Nos. 2009-044099 filed on Feb. 26, 2009 and 2009-082685 filed on Mar. 30, 2009, the entire contents of which are hereby incorporated by reference.

FIELD OF THE INVENTION

The present invention relates to a reagent preparing device, a specimen processing system, and a reagent preparing method.

BACKGROUND OF THE INVENTION

A reagent preparing device capable of preparing the reagent from a plurality of different liquids is conventionally known (see e.g., U.S. Pat. No. 5,800,056).

U.S. Pat. No. 5,800,056 discloses a reagent preparing device including a reagent quantifying tank for accommodating a high concentration reagent, a pure water quantifying tank for accommodating pure water, a preparing tank, connected to the reagent quantifying tank and the pure water quantifying tank, for preparing a reagent, a storage tank, connected to the preparing tank, for accommodating the prepared reagent, and a supply tank, connected to the storage tank, for waiting for the supply of reagent to a measurement section. The reagent preparing device prepares the reagent by supplying the high concentration reagent quantified to a predetermined amount and the pure water quantified to a predetermined amount to the preparing tank, and stirring the same in the preparing tank. After the reagent preparation is completed, all reagents prepared in the preparing tank is transferred to the storage tank. Thereafter, when the transfer of the prepared reagent is completed, the preparation of the reagent is resumed. The reagent is stored in the storage tank by repeating such operation.

However, the reagent preparing device of U.S. Pat. No. 5,800,056 is demanded to increase the amount of reagent prepared within a predetermined time.

SUMMARY OF THE INVENTION

The scope of the present invention is defined solely by the appended claims, and is not affected to any degree by the statements within this summary.

A first aspect of the present invention is a reagent preparing device capable of supplying a mixed solution, including a first liquid and a second liquid, to a measurement section for measuring a specimen using the mixed solution as a reagent, the reagent preparing device comprising: a first mixed solution container for accommodating the mixed solution; a second mixed solution container for accommodating the mixed solution; and a controller for controlling supply of the first liquid and the second liquid to supply the first liquid and the second liquid to the first mixed solution container, and to supply the first liquid and the second liquid to the second mixed solution container.

A second aspect of the present invention is a specimen processing system comprising: a measurement section for measuring a specimen using a predetermined mixed solution including a first liquid and a second liquid as a reagent; a first mixed solution container for accommodating the mixed solution; a second mixed solution container for accommodating the mixed solution; and a controller for controlling supply of the first liquid and the second liquid to supply the first liquid and the second liquid to the first mixed solution container, and to supply the first liquid and the second liquid to the second mixed solution container.

A third aspect of the present invention is a reagent preparing method for preparing a mixed solution, including a first liquid and a second liquid, to be supplied to a measurement section for measuring a specimen using the mixed solution as a reagent, the reagent preparing method comprising: (a) supplying the first liquid and the second liquid to a first mixed solution container; and (b) supplying the first liquid and the second liquid to a second mixed solution container; wherein the (a) and (b) are alternately executed.

DETAILED DESCRIPTION OF THE PREFERRED EMBODIMENTS

The preferred embodiments of the present invention will be described hereinafter with reference to the drawings.

First Embodiment

First, a configuration of a blood analyzer 1 according to a first embodiment of the present invention will be described with reference to FIGS. 1 to 14. In the first embodiment, a case of using the reagent preparing device 4 according to the first embodiment of the present invention as one part of a blood analyzer 1 for performing a blood test will be described. In the present specification, the term "mixed solution" is used in a wide concept including a solution in a state the first liquid and the second liquid are simply mixed, and a solution in which stirring is carried out from the state the first liquid and the second liquid are mixed to a state of having a uniform concentration (state prepared as reagent).

Figure 1:
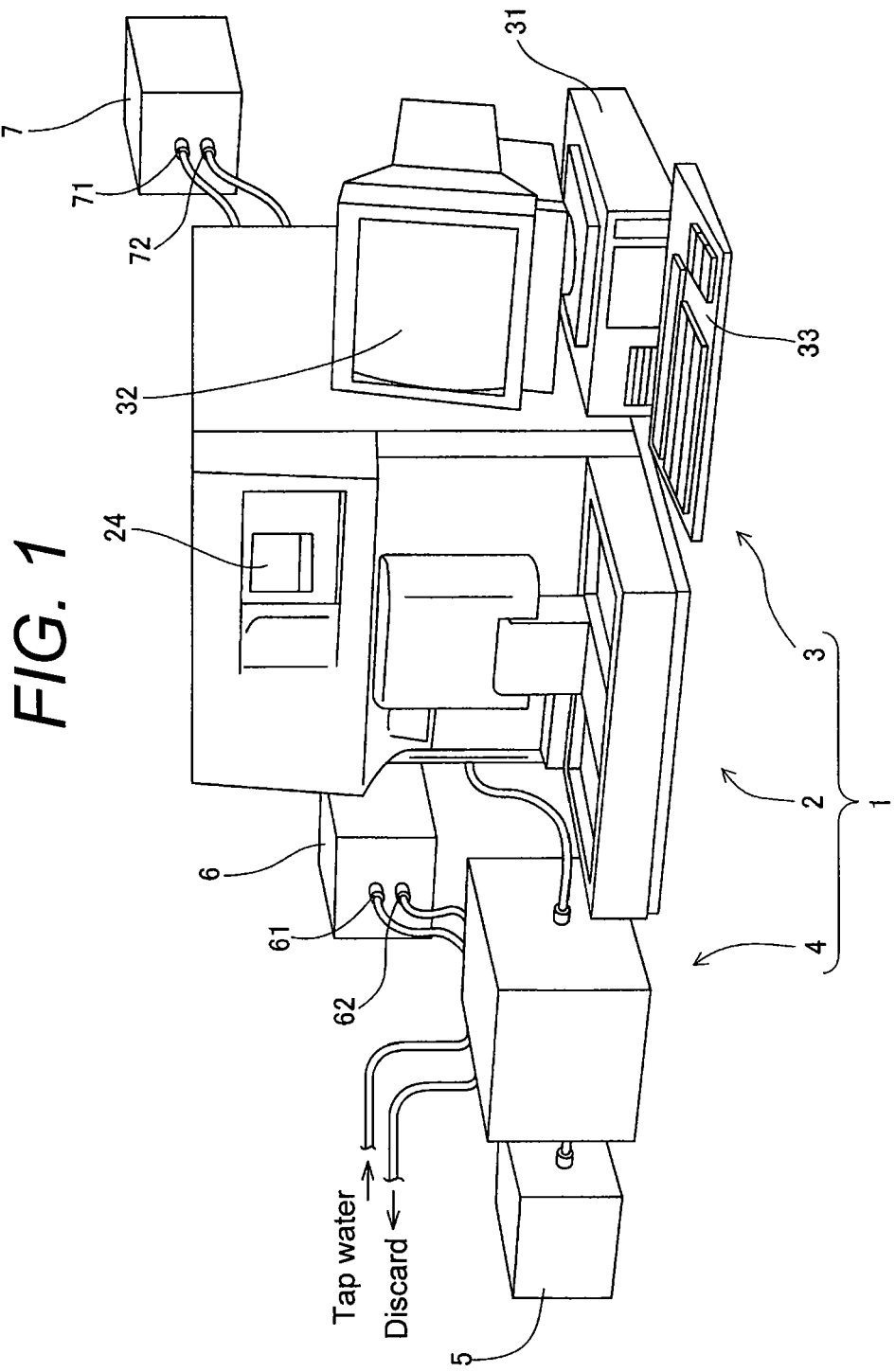
FIG. 1 is a perspective view showing a blood analyzer including a reagent preparing device according to a first embodiment of the present invention.

As shown in FIG. 1, the blood analyzer 1 is configured by a measurement section 2 having a function of measuring the blood, a data processing section 3 for analyzing the measurement data output from the measurement section 2 and obtaining an analysis result, and the reagent preparing device 4 for preparing a reagent for use in the processing of a specimen. The measurement section 2 is configured to perform measurements on white blood cells, reticulocytes, and blood platelets in the blood through a flow cytometry method. The measurement section 2 is configured to dilute the blood using a reagent prepared and supplied by the reagent preparing device 4 and to perform measurements on white blood cells, reticulocytes, and blood platelets. The measurement section 2 is also configured to clean a sampling valve 21b, a reaction chamber 21c and the like arranged in a sample preparing unit 21, as well as a sheath flow cell 22c and the like arranged in a detection unit 22, which are to be hereinafter described, using the reagent prepared and supplied by the reagent preparing device 4 as a cleaning fluid. The flow cytometry method is a measurement method of particles (blood cells) for detecting the forward scattered light, the lateral scattered light, and the lateral fluorescence emitted by the particles (blood cells) in the measurement sample by forming a sample flow including the measurement sample and irradiating the sample flow with laser light.

Figure 2:
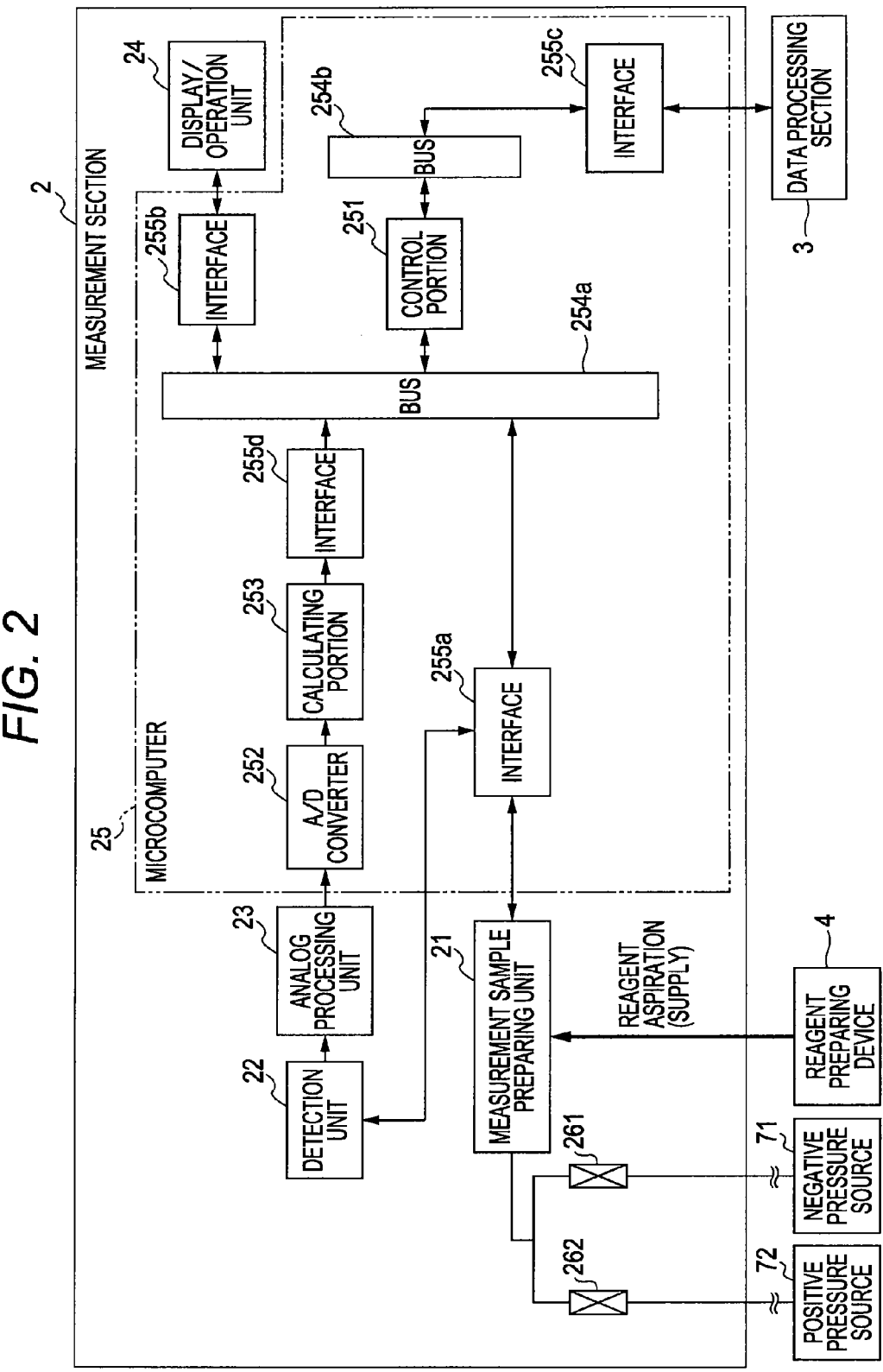
FIG. 2 is a block diagram showing a configuration of the blood analyzer including the reagent preparing device according to the first embodiment shown in FIG. 1.

As shown in FIG. 2, the measurement section 2 includes a measurement sample preparing unit 21, a detection unit 22 for performing a measurement of the measurement sample, an analog processing unit 23 with respect to the output of the detection unit 22, a display/operation unit 24, and a microcomputer 25 for controlling the measurement section 2. The measurement section 2 also includes a pneumatic unit 7 (see FIG. 1) installed at the exterior of the housing, and is configured to send each liquid in the device using negative pressure and positive pressure supplied from the pneumatic unit 7. The pneumatic unit 7 includes a negative pressure source 71 for supplying negative pressure and a positive pressure source 72 for supplying positive pressure to the measurement section 2.

Figure 3:
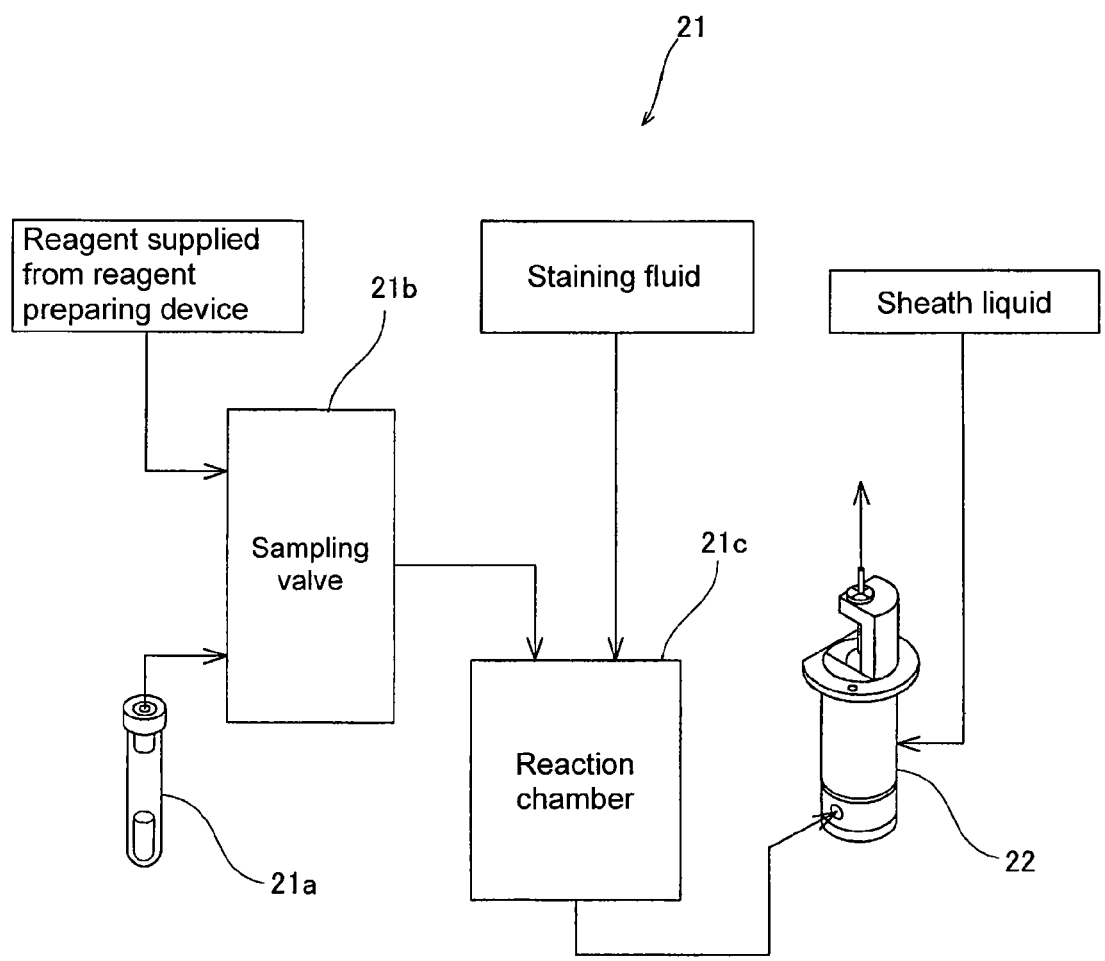
FIG. 3 is a view describing a sample preparing unit of the blood analyzer including the reagent preparing device according to the first embodiment shown in FIG. 1.

The measurement sample preparing unit 21 is arranged to prepare a white blood cell measurement sample, a reticulocyte measurement sample, and a blood platelet measurement sample. As shown in FIG. 3, the measurement sample preparing unit 21 includes the sampling valve 21b for aspirating blood and the reaction chamber 21c. A blood collecting tube 21a stores the blood to be analyzed. As shown in FIG. 2, the measurement sample preparing unit 21 is connected to the negative pressure source 71 through an electromagnetic valve 261, and connected to the positive pressure source 72 through an electromagnetic valve 262. When the electromagnetic valve 261 is opened with the electromagnetic valve 262 closed, the negative pressure is supplied from the negative pressure source 71 to the measurement sample preparing unit 21. The reagent to be used for the measurement is then aspirated from the reagent preparing device 4 (reagent is supplied from the reagent preparing device 4).

The sampling valve 21b has a function of quantifying the blood of the blood collecting tube 21a aspirated by an aspiration pipette (not shown) by a predetermined amount. The sampling valve 21b is configured so that a predetermined reagent can be mixed with the aspirated blood. That is, the sampling valve 21b is configured so that a diluted sample in which a predetermined amount of reagent supplied from the reagent preparing device 4 is mixed in a predetermined amount of blood can be generated.

The reaction chamber 21c is configured so that a predetermined staining fluid is further mixed to the diluted sample supplied from the sampling valve 21b and reacts with it for a predetermined time. The measurement sample preparing unit 21 thus has a function of preparing the white blood cell measurement sample in which the white blood cells are stained and the red blood cells are hemolyzed. The measurement sample preparing unit 21 also has a function of preparing the reticulocyte measurement sample in which the reticulocyte is stained and a function of preparing the blood platelet measurement sample in which the blood platelet is stained.

The measurement sample preparing unit 21 is also configured to supply the white blood cell measurement sample with the sheath liquid from the measurement sample preparing unit 21 to the sheath flow cell 22c described later (see FIG. 4) at the time of a white blood cell differential measurement (hereinafter also referred to as "DIFF measurement") mode. The measurement sample preparing unit 21 is also configured to supply the reticulocyte measurement sample with the sheath liquid from the measurement sample preparing unit 21 to the sheath flow cell 22c at the time of a reticulocyte measurement (hereinafter also referred to as "RET measurement") mode. Furthermore, the measurement sample preparing unit 21 is also configured to supply the blood platelet measurement sample with the sheath liquid from the measurement sample preparing unit 21 to the sheath flow cell 22c at the time of a blood platelet measurement (hereinafter also referred to as "PLT measurement") mode.

Figure 4:
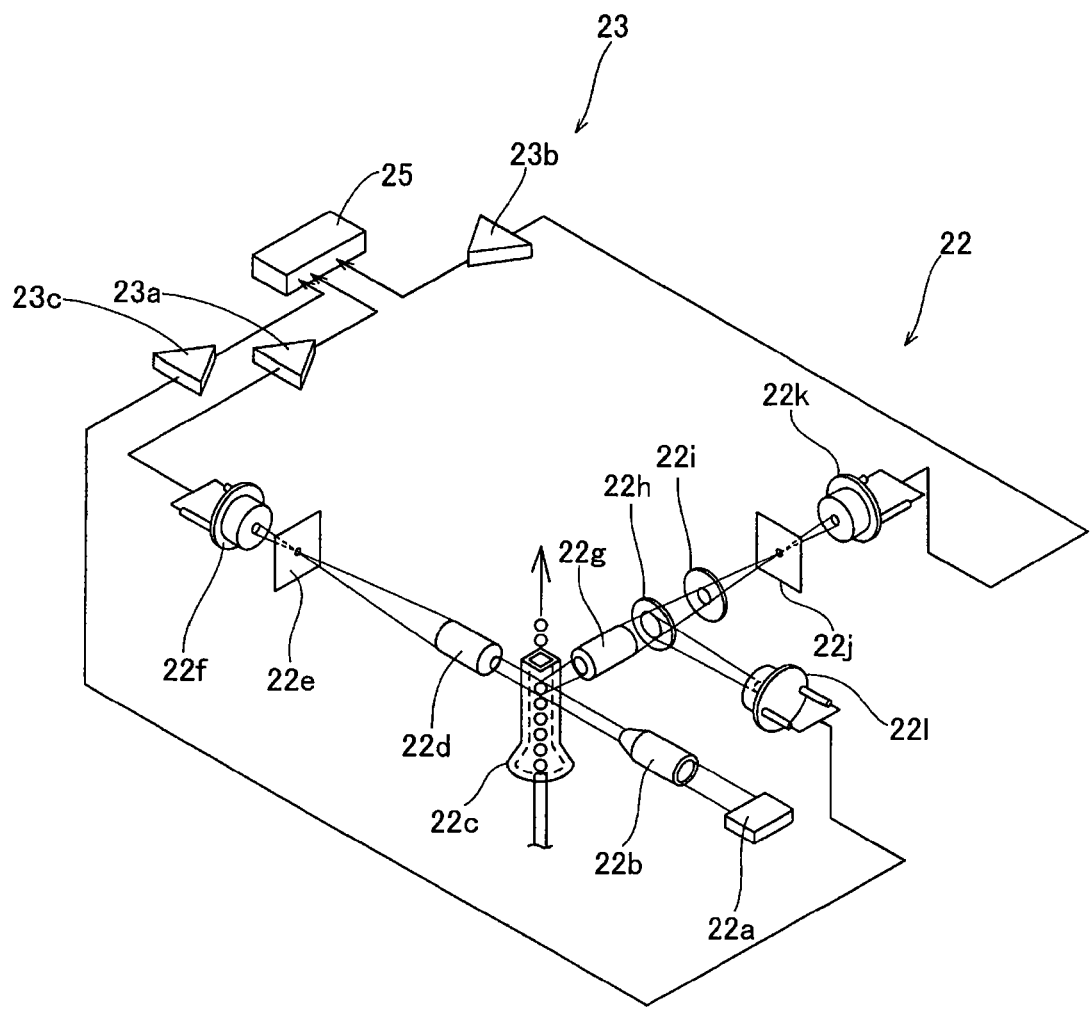
FIG. 4 is a schematic view showing a detection unit of the blood analyzer including the reagent preparing device according to the first embodiment shown in FIG. 1.

As shown in FIG. 4, the detection unit 22 includes a light emitting portion 22a for emitting laser light, an irradiation lens unit 22b, the sheath flow cell 22c irradiated with laser light, a light collecting lens 22d arranged on an extended line in a direction the laser light emitted from the light emitting portion 22a advances, a pin hole 22e and a PD (Photo Diode) 22f, a light collecting lens 22g arranged in a direction intersecting the direction the laser light emitted from the light emitting portion 22a advances, a dichroic mirror 22h, an optical filter 22i, a pin hole 22j and an APD (Avalanche Photo Diode) 22k, and a PD 22l arranged at the side of the dichroic mirror 22h.

The light emitting portion 22a is arranged to emit light to the sample flow including the measurement sample that passes the inside of the sheath flow cell 22c. The irradiation lens unit 22b is arranged to convert the light emitted from the light emitting portion 22a to parallel light. The PD 22f is arranged to receive the forward scattered light output from the sheath flow cell 22c. The information on the size of the particle (blood cell) in the measurement sample can be obtained from the forward scattered light output from the sheath flow cell 22c.

The dichroic mirror 22h is arranged to separate the lateral scattered light and the lateral fluorescence output from the sheath flow cell 22c. Specifically, the dichroic mirror 22h is arranged to have the lateral scattered light output from the sheath flow cell 22c enter to the PD 22l, and to have the lateral fluorescence output from the sheath flow cell 22c enter to the APD 22k. The PD 22l is arranged to receive the lateral scattered light. Internal information, for example, the size of the core of the particle (blood cell) in the measurement sample can be obtained from the lateral scattered light output from the sheath flow cell 22c. The APD 22k is arranged to receive the lateral fluorescence. Information on the staining degree of the particle (blood cell) in the measurement sample can be obtained from the lateral fluorescence output from the sheath flow cell 22c. The PD 22f, 22l, and the APD 22k respectively have a function of converting the received optical signal to an electrical signal.

As shown in FIG. 4, the analog processing unit 23 includes amplifiers 23a, 23b, and 23c. The amplifiers 23a, 23b, and 23c are respectively arranged to perform amplification and waveform processing on the electrical signal output from the PD 22f, 22l, and the APD 22k.

As shown in FIG. 2, the microcomputer 25 includes a control portion 251 including a control processor and a memory for operating the control processor, an A/D converter 252 for converting a signal output from the analog processing unit 23 to a digital signal, and a calculating portion 253 for performing a predetermined process on the digital signal output from the A/D converter 252.

The control portion 251 has a function of controlling the measurement sample preparing unit 21 and the detection unit 22 through a bus 254a and an interface 255a. The control portion 251 is connected with the display/operation unit 24 through the bus 254a and an interface 255b, and connected with the data processing section 3 through a bus 254b and an interface 255c. The calculating portion 253 has a function of outputting a calculation result to the control portion 251 through an interface 255d and the bus 254a. The control portion 251 has a function of transmitting the calculation result (measurement data) to the data processing section 3.

Figure 5:
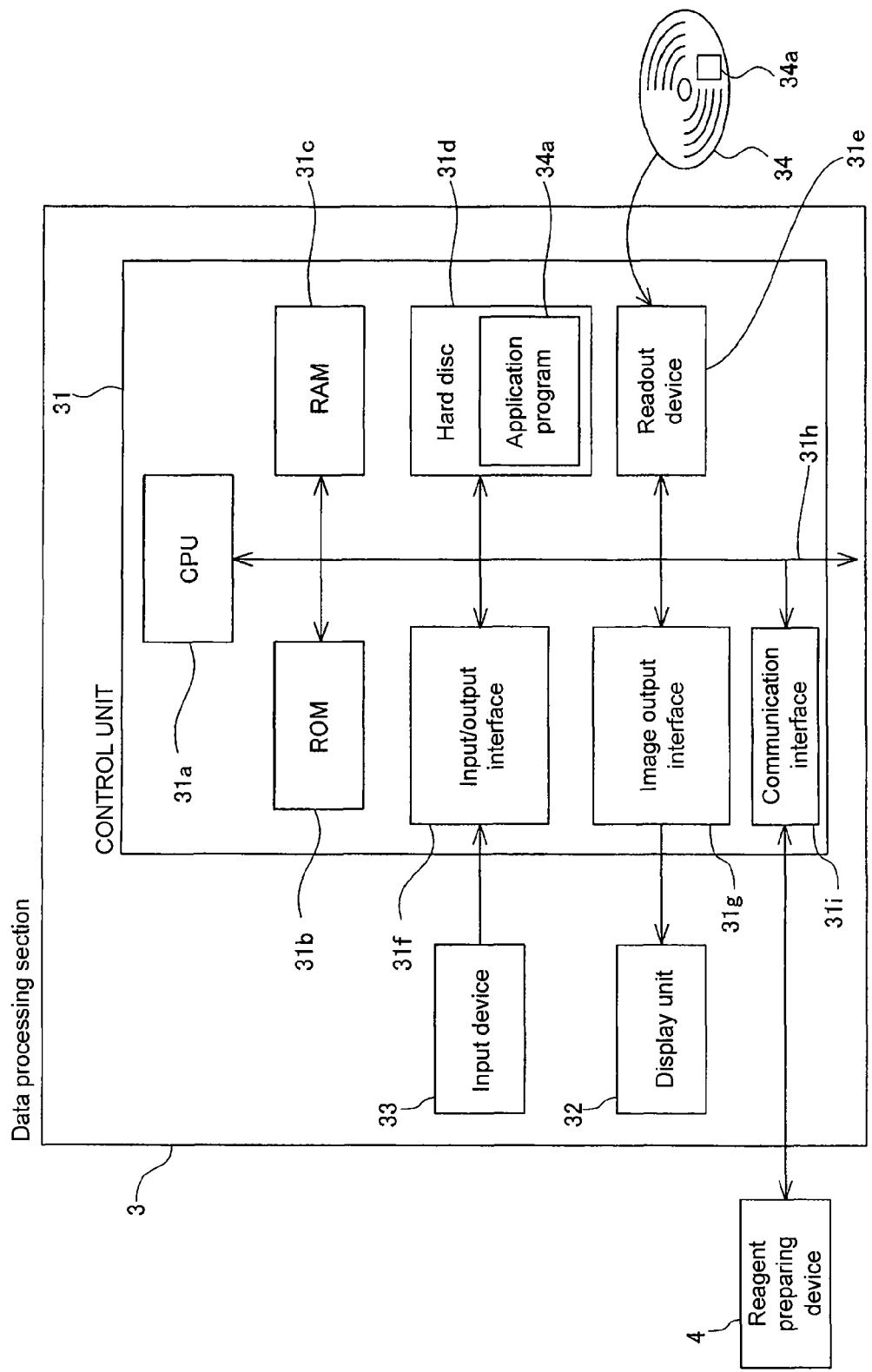
FIG. 5 is a block diagram showing a configuration of a data processing section of the blood analyzer including the reagent preparing device according to the first embodiment shown in FIG. 1.

As shown in FIG. 1, the data processing section 3 includes a personal computer (PC) and the like, and has a function of analyzing the measurement data of the measurement section 2 and displaying the analysis result. The data processing section 3 includes a control unit 31, a display unit 32, and an input device 33, as shown in FIG. 5.

The control unit 31 has a function of transmitting a measurement start signal including the measurement mode information and a shutdown signal to the measurement section 2. As shown in FIG. 5, the control unit 31 is also configured by a CPU 31a, a ROM 31b, a RAM 31c, a hard disc 31d, a readout device 31e, an input/output interface 31f, an image output interface 31g and a communication interface 31i. The CPU 31a, the ROM 31b, the RAM 31c, the hard disc 31d, the readout device 31e, the input/output interface 31f, the image output interface 31g and the communication interface 31i are connected by a bus 31h.

The CPU 31a is arranged to execute computer programs stored in the ROM 31b and the computer programs loaded in the RAM 31c. The ROM 31b is configured by mask ROM, PROM, EPROM, EEPROM, and the like, and is recorded with computer programs to be executed by the CPU 31a, data used for the same, and the like.

The RAM 31c is configured by SRAM, DRAM and the like. The RAM 31c is used to read out the computer programs recorded on the ROM 31b and the hard disc 31d. The RAM 31c is used as a work region of the CPU 31a when executing the computer programs.

The hard disc 31d is installed with various computer programs to be executed by the CPU 31a such as operating system and application program, as well as data used in executing the computer program. The application program 34a described later is also installed in the hard disc 31d.

The readout device 31e is configured by flexible disc drive, CD-ROM drive, DVD-ROM drive and the like, and is able to read out computer programs and data recorded on a portable recording medium 34. The application program 34a causing the computer to implement a predetermined function is stored in the portable recording medium 34. The computer serving as the data processing section 3 reads out the application program 34a from the portable recording medium 34, and installs the application program 34a to the hard disc 31d.

The application program 34a is not only provided by the portable recording medium 34, and may be provided through an electrical communication line (wired or wireless) from external devices communicably connected with the data processing section 3 by the electrical communication line. For instance, the application program 34a may be stored in the hard disc of the server computer on the Internet, wherein the data processing section 3 can access the server computer to download the application program 34a and install the application program 34a in the hard disc 31d.

Operating system providing graphical user interface environment such as Windows (registered trademark) manufactured and sold by US Microsoft Co. is installed in the hard disc 31d. In the following description, the application program 34a according to the first embodiment is assumed to be operating on the operating system.

The input/output interface 31f is configured by serial interface such as USB, IEEE1394 and RS-232C; parallel interface such as SCSI, IDE and IEEE 1284; analog interface such as a D/A converter and an A/D converter, and the like. The input device 33 including a keyboard and a mouse is connected to the input/output interface 31f, so that the user can input data to the data processing section 3 using the input device 33. The user can also select the measurement mode, and activate and shut down the measurement section 2 and the reagent preparing device 4 using the input device 33. For instance, when the user instructs to activate or shut down using the input device 33, an activation signal or a shut down signal is transmitted to the reagent preparing device 4 through the communication interface 31i.

The image output interface 31g is connected to the display unit 32 configured by LCD, CRT or the like, and is configured to output a video signal corresponding to the image data provided from the CPU 31a to the display unit 32. The display unit 32 displays the image (screen) according to the input video signal.

In the first embodiment, the reagent preparing device 4 is arranged to prepare the reagent to be used in the measurement sample preparing unit 21 of the measurement section 2. Specifically, the reagent preparing device 4 is configured to prepare the reagent used in blood analysis by diluting a high concentration reagent (stock solution of the reagent) to a desired concentration using the RO water produced from the tap water. The RO water is one type of pure water and is water in which impurities are removed by being transmitted through an RO (Reverse Osmosis) membrane (reverse osmosis membrane). Other than the RO water, the pure water includes purified water, deionized water and distilled water, and is water subjected to the process of removing impurities, and the purity is not particularly limited.

Figure 6:
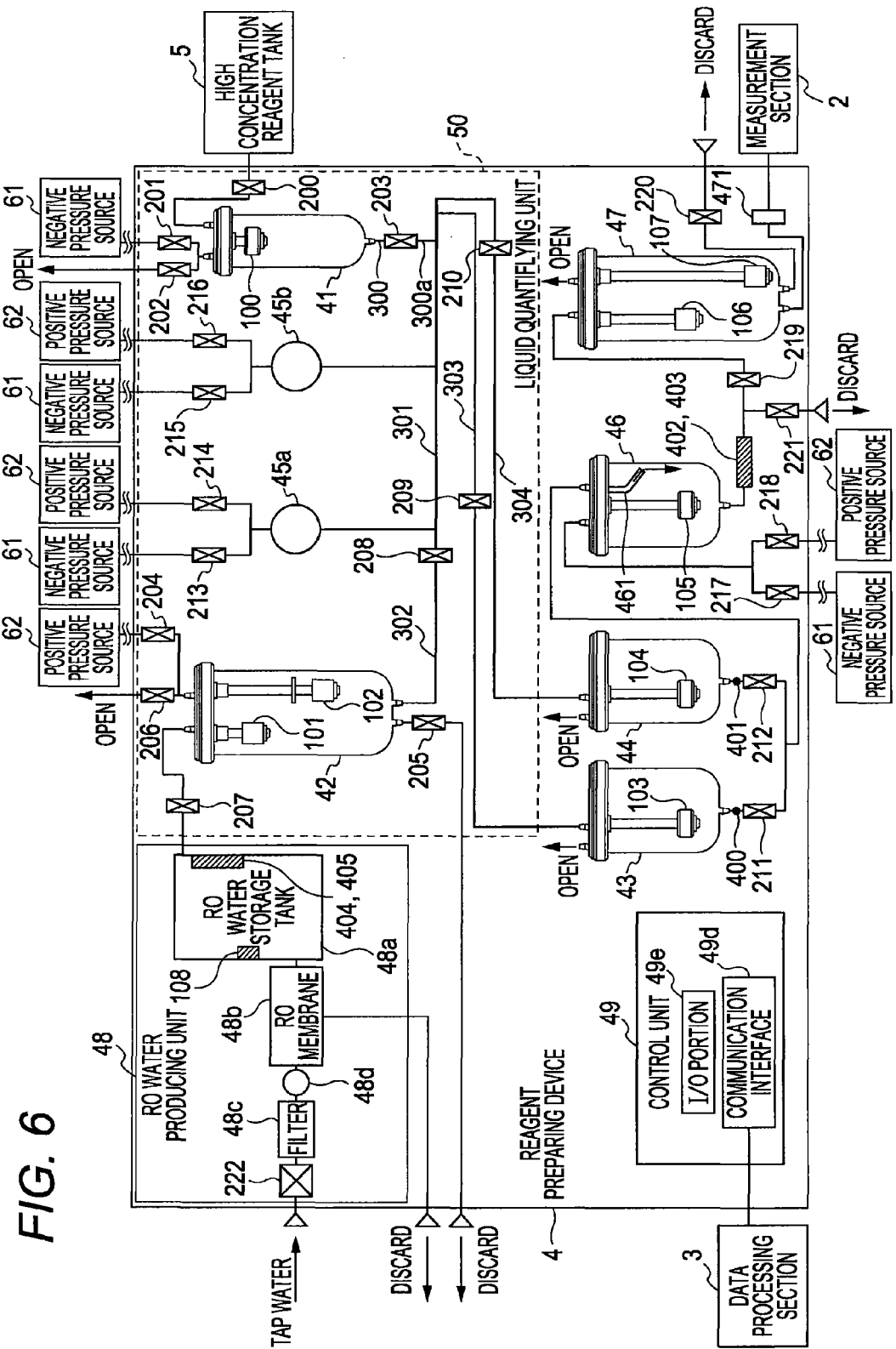
FIG. 6 is a block diagram showing a configuration of the reagent preparing device according to the first embodiment shown in FIG. 1.

As shown in FIG. 6, the reagent preparing device 4 includes a high concentration reagent chamber 41, a RO water chamber 42, a first diluting chamber 43 and a second diluting chamber 44, two diaphragm pumps 45a and 45b, a stirring chamber 46, a supply chamber 47, a RO water producing unit 48, and a control unit 49 for controlling each unit of the reagent preparing device 4. The reagent preparing device 4 also includes a pneumatic unit 6 (see FIG. 1) installed at the exterior of the housing, and is configured to send each liquid in the device using negative pressure and positive pressure supplied from the pneumatic unit 6. The pneumatic unit 6 includes a negative pressure source 61 for supplying negative pressure and a positive pressure source 62 for supplying positive pressure to the reagent preparing device 4.

The high concentration reagent chamber 41 is configured to supply the high concentration reagent from a high concentration reagent tank 5. The high concentration reagent chamber 41 includes a float switch 100 for detecting that a predetermined amount of high concentration reagent is stored in the chamber. The float switch 100 is configured such that the float portion moves up and down according to the liquid amount (liquid level) in the high concentration reagent chamber 41. Each unit is controlled by the control unit 49 such that the high concentration reagent is supplied from the high concentration reagent tank 5 to the high concentration reagent chamber 41 when the float portion of the float switch 100 reaches the lower limit. Furthermore, each unit is controlled by the control unit 49 such that the supply of the high concentration reagent from the high concentration reagent tank 5 to the high concentration reagent chamber 41 is stopped when the float portion of the float switch 100 reaches the upper limit. The float switch 100 is arranged near the upper end of the high concentration reagent chamber 41, and is configured such that the float portion reaches the upper limit when about 300 mL of the high concentration reagent is stored in the high concentration reagent chamber 41. The high concentration reagent is thus supplied such that about 300 mL is stored in the high concentration reagent chamber 41 on a constant basis.

The high concentration reagent chamber 41 is connected to the high concentration reagent tank 5 through an electromagnetic valve 200, and is connected to the negative pressure source 61 of the pneumatic unit 6 through an electromagnetic valve 201. The high concentration reagent chamber 41 is also configured to be opened to atmosphere or closed by the opening and closing of the electromagnetic valve 202. The high concentration reagent chamber 41 is also connected to a flow path 301 for transferring the liquid from the diaphragm pump 45a (45b) to the first diluting chamber 43 (second diluting chamber 44) by the flow path 300. An electromagnetic valve 203 is arranged on the flow path 300, which electromagnetic valve 203 is arranged near the flow path 301. Specifically, the length of the flow path 300a between the electromagnetic valve 203 and the flow path 301 is set to a small length of about 15 mm. The flow path 300 (300a) connected to the high concentration reagent chamber 41 has an inner diameter of about 1.8 mm, and the flow path 301 has an inner diameter of about 4.0 mm.

The high concentration reagent contains antiseptic. The antiseptic agent may be (sodium-2-pyridylthio-1-oxide), and may be an antiseptic agent in which TKM-A (manufactured by API Co.) contains (sodium-2-pyridylthio-1-oxide).

The RO water chamber 42 is configured such that the RO water for diluting the high concentration reagent is supplied from the RO water producing unit 48.

The RO water chamber 42 includes float switches 101 and 102 for detecting that the RO water stored in the chamber has reached the upper limit amount and the lower limit amount, respectively. The float switch 101 (102) is configured such that the float portion moves up and down according to the liquid amount (liquid level) in the RO water reagent chamber 42. Each unit is controlled by the control unit 49 such that the supply of RO water from the RO water producing unit 48 to the RO water chamber 42 is stopped when the float portion of the float switch 101 reaches the position corresponding to the upper limit amount. Furthermore, each unit is controlled by the control unit 49 such that the RO water is supplied from the RO water producing unit 48 to the RO water chamber 42 when the float portion of the float switch 102 reaches the position corresponding to the lower limit amount. The float switch 101 is arranged near the upper end of the RO water chamber 42, and is configured such that the float portion reaches the position corresponding to the upper limit amount of the RO water chamber 42 when about 600 mL of the RO water is stored in the RO water chamber 42. The float switch 102 is configured such that the float portion reaches the position corresponding to the lower limit amount of the RO water chamber 42 when the RO water stored in the RO water chamber 42 reduces to about 300 mL. The RO water of greater than or equal to about 300 mL and less than or equal to about 600 mL is thus stored in the RO water chamber 42 while the reagent preparing device 4 is operating.

The RO water chamber 42 is configured so that the RO water in the chamber can be discarded. Specifically, the RO water chamber 42 is connected to the positive pressure source 62 through the electromagnetic valve 204 and connected to a discard flow path through the electromagnetic valve 205, so that the RO water inside is pushed out to the discard flow path by the positive pressure force by opening both electromagnetic valves 204 and 205. The RO water chamber 42 is configured to be opened to atmosphere and closed by the opening and closing of the electromagnetic valve 206. The RO water chamber 42 is connected to the RO water storage tank 48a, to be hereinafter described, of the RO water producing unit 48 through the electromagnetic valve 207. The RO water chamber 42 is connected to the diaphragm pumps 45a and 45b by the flow path 302 through the electromagnetic valve 208.

The first diluting chamber 43 and the second diluting chamber 44 are respectively arranged to dilute the high concentration reagent with the RO water. As hereinafter described, the first diluting chamber 43 (second diluting chamber 44) is configured to accommodate about 300 mL of liquid (mixed solution of high concentration reagent and RO water) sent by the diaphragm pumps 45a and 45b. The first diluting chamber 43 and the second diluting chamber 44 can accommodate the about 300 mL of liquid (mixed solution) as a maximum liquid amount and have substantially the same capacity (e.g., about 350 mL). The first diluting chamber 43 (second diluting chamber 44) includes a float switch 103 (104) for detecting that the remaining amount of the liquid (mixed solution of high concentration reagent and RO water) accommodated in the chamber reached a predetermined amount. The float switch 103 (104) is configured such that the float portion moves up and down according to the liquid amount (liquid level) in the first diluting chamber 43 (second diluting chamber 44). The first diluting chamber 43 (second diluting chamber 44) is configured so as to be always opened to atmosphere. The first diluting chamber 43 (second diluting chamber 44) is connected to the flow path 301 by the flow path 303 (304) through the electromagnetic valve 209 (210). The flow path 303 (304) has an inner diameter of about 4 mm, similar to the flow path 301. The liquid (RO water and high concentration reagent) transferred through the flow path 301 can be transferred to the first diluting chamber 43 by opening the electromagnetic valve 209 with the electromagnetic valve 210 closed. The liquid (RO water and high concentration reagent) transferred through the flow path 301 can be transferred to the second diluting chamber 44 by opening the electromagnetic valve 210 with the electromagnetic valve 209 closed. In other words, the electromagnetic valves 209 and 210 are respectively configured to function as a flow path switching unit of the flow paths 303 and 304. In the first embodiment, each unit is controlled by the control unit 49 so that the supplying operation of the RO water and the high concentration reagent to the first diluting chamber 43 and the supplying operation of the RO water and the high concentration reagent to the second diluting chamber 44 are alternately performed by the switching of the flow paths 303 and 304.

The first diluting chamber 43 (second diluting chamber 44) is connected to the stirring chamber 46 through the electromagnetic valve 211 (212). An air bubble sensor 400 (401) is arranged between the first diluting chamber 43 (second diluting chamber 44) and the electromagnetic valve 211 (212). The air bubble sensor 400 (401) is a transmissive sensor, and is configured to detect air bubbles that pass the flow path. Detection that the liquid (mixed solution of high concentration reagent and RO water) in the first diluting chamber 43 (second diluting chamber 44) are all discharged (supplied) can be checked by the control unit 49 when the float portion of the float switch 103 (104) reaches the lower limit and the air bubbles are detected by the air bubble sensor 400 (401). The total amount (about 300 mL) of the mixed solution accommodated in the first diluting chamber 43 (second diluting chamber 44) is supplied to the stirring chamber 46 at the time of the supply of the mixed solution in the first diluting chamber 43 (second diluting chamber 44). When the first diluting chamber 43 (second diluting chamber 44) becomes empty (all liquid in the chamber is discharged), each unit is controlled by the control unit 49 so that the high concentration reagent and the RO water are supplied to the empty first diluting chamber 43 (second diluting chamber 44).

The diaphragm pumps 45a and 45b have similar configuration with respect to each other, and are configured to perform the same operation at the same time. That is, the diaphragm pumps 45a and 45b are controlled by the control unit 49 so that the timing of the supplying operation substantially coincide. The diaphragm pump 45a (45b) has a function of quantifying about 6.0 mL (constant amount) of the high concentration reagent and the RO water in one quantifying operation. A total of about 12 mL (about 6.0 mL×2) of liquid is supplied by one quantification for the supply amount of the liquid (high concentration reagent and RO water). The diaphragm pump 45a (45b) is connected to the negative pressure source 61 through the electromagnetic valve 213 (215), and also connected to the positive pressure source 62 through the electromagnetic valve 214 (216).

The detailed configuration of the diaphragm pump 45a (45b) will now be described. In the first embodiment, the diaphragm pumps 45a and 45b have similar configuration with respect to each other, and thus the diaphragm pump 45a will be described as a representative, and the detailed description of the diaphragm pump 45b will be omitted.

Figure 7:
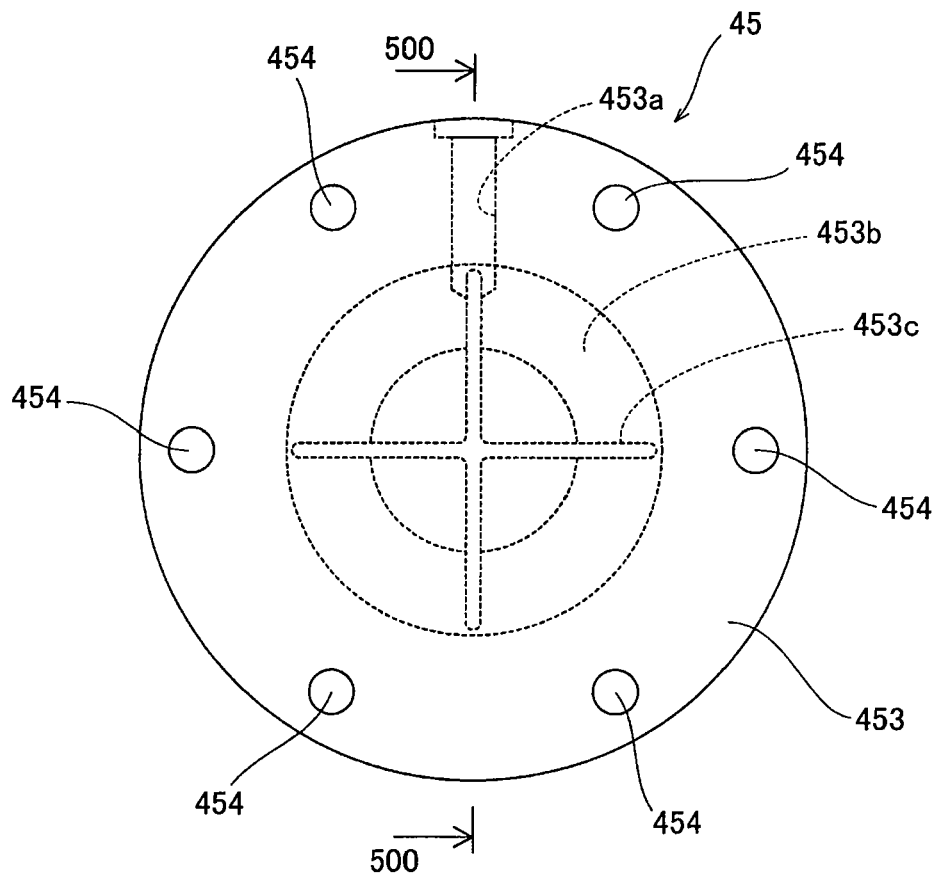
FIG. 7 is a plan view showing a diaphragm pump of the reagent preparing device according to the first embodiment shown in FIG. 1.
Figure 8:
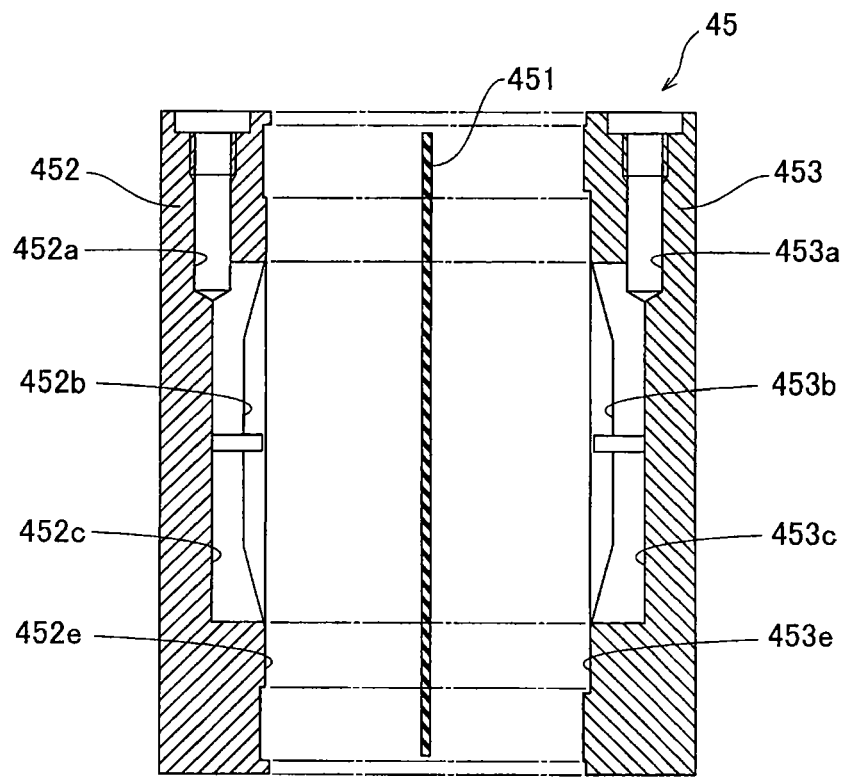
FIG. 8 is an exploded view at a cross-section taken along a line 500-500 of FIG. 7.
Figure 9:
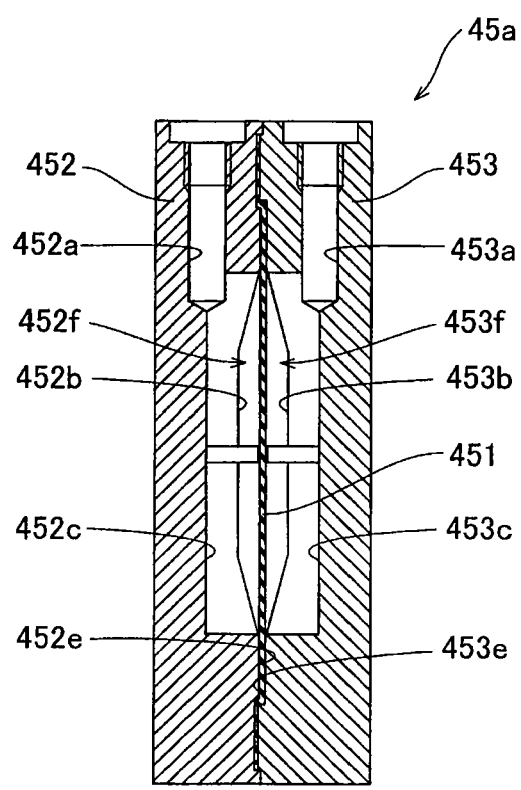
FIG. 9 is a cross-sectional view taken along the line 500-500 of FIG. 7.

As shown in FIG. 7, the diaphragm pump 45a has a circular shape in plan view. As shown in FIGS. 8 and 9, the diaphragm pump 45a includes a membrane body 451 made of rubber material such as EPDM, and a pair of case pieces 452 and 453 configured to sandwich the membrane body 451 from both sides.

Figure 10:
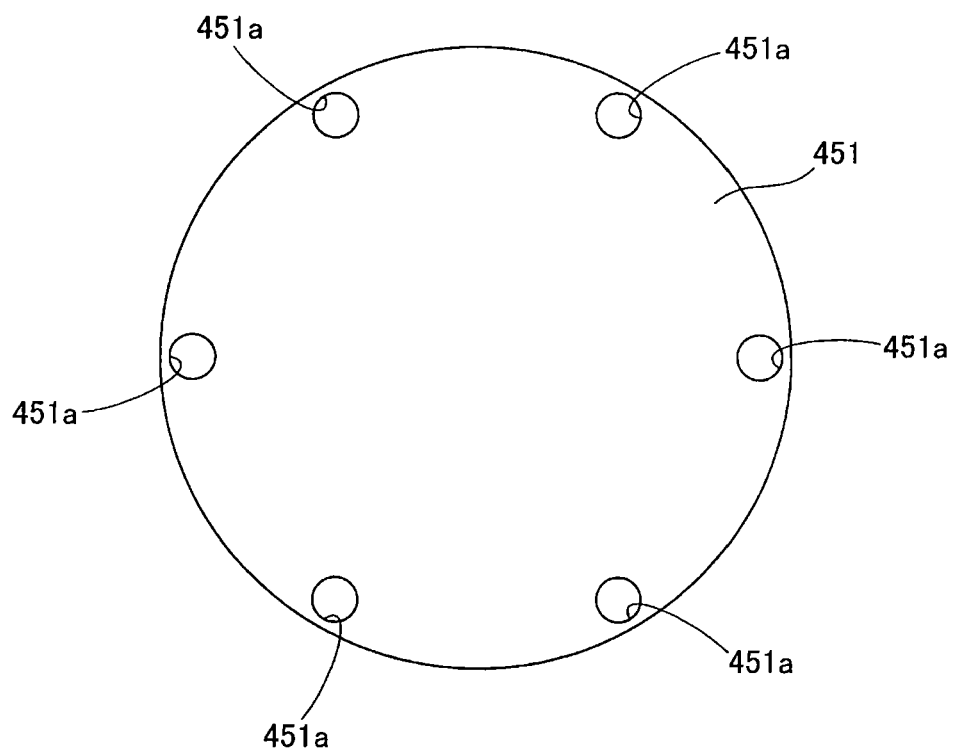
FIG. 10 is a plan view showing a film body of the diaphragm pump of the reagent preparing device according to the first embodiment shown in FIG. 1.

As shown in FIG. 10, the membrane body 451 is formed to a flat plate shape having a circular shape when seen in plan view, and includes six screw holes 451a for passing a screw 454. As shown in FIGS. 8 and 9, the membrane body 451 is also configured to be sandwiched by the case pieces 452 and 453 from both sides.

Figure 11:
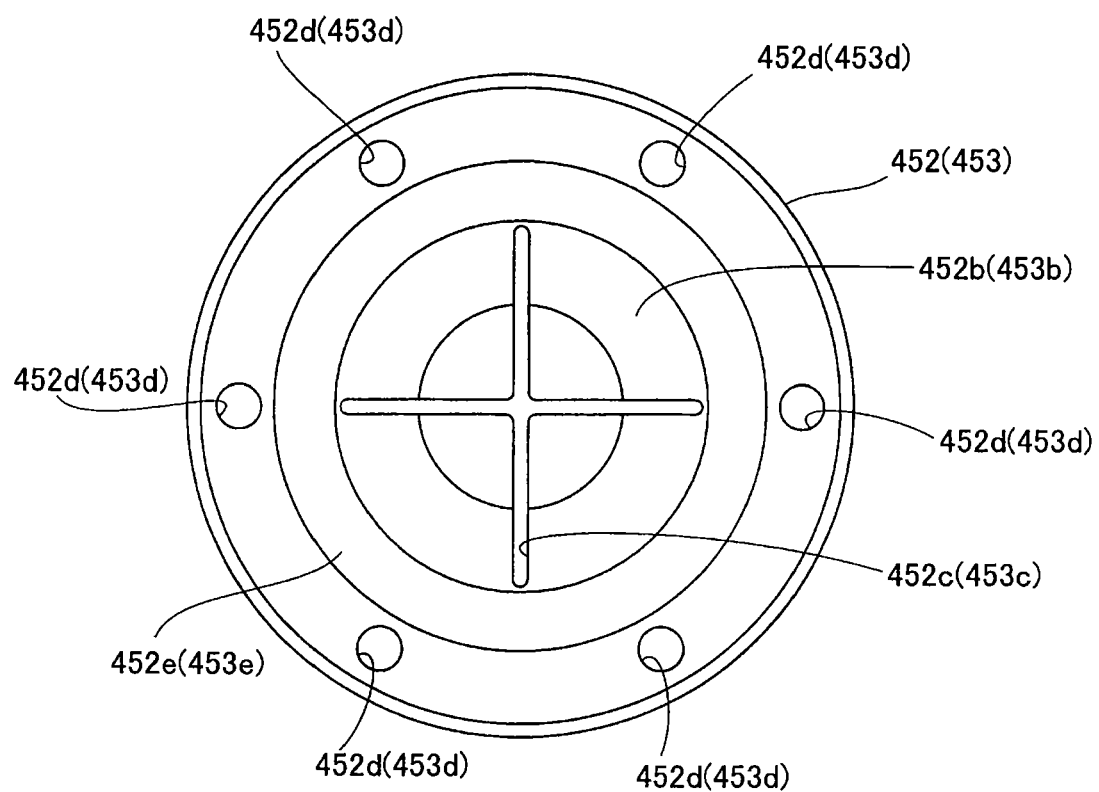
FIG. 11 is a plan view describing an internal structure of the diaphragm pump of the reagent preparing device according to the first embodiment shown in FIG. 1.

As shown in FIGS. 8, 9, and 11, the case piece 452 includes a flow port 452a (see FIGS. 8 and 9), an inner wall 452b formed to a circular truncated cone shape, a cross-shaped groove 452c arranged at substantially the middle of the inner wall 452b when seen in plan view, six screw holes 452d (see FIG. 11), and a ring-shaped sandwiching portion 452e formed to surround the inner wall 452b when seen in plan view. As shown in FIGS. 8, 9, and 11, the case piece 453 is formed similar to the case piece 452, and a flow port 453a (see FIGS. 8 and 9), an inner wall 453b, a groove 453c, a screw hole 453d (see FIG. 11) and a sandwiching portion 453e, respectively, correspond to the flow port 452a, the inner wall 452b, the groove 452c, the screw hole 452d and the sandwiching portion 452e.

As shown in FIG. 9, the case pieces 452 and 453 are joined to each other with six screws 454 (see FIG. 7) with the membrane body 451 sandwiched with the sandwiching portions 452e and 453e. A chamber portion 452f surrounded by the inner wall 452b and the membrane body 451, and a chamber portion 453f surrounded by the inner wall 453b and the membrane body 451 are thereby formed. The flow port 452a and the chamber portion 452f are spatially connected to each other through the groove 452c, and the flow port 453a and the chamber portion 453f are spatially connected to each other through the groove 453c. The chamber portions 452f and 453f are spatially separated from each other by the membrane body 451.

Figure 12:
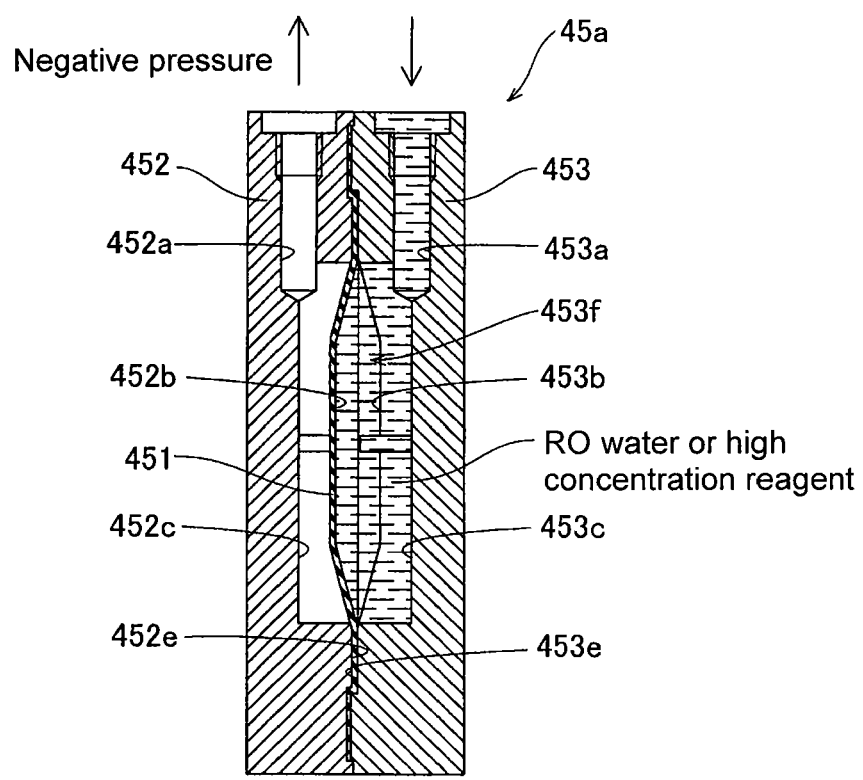
FIG. 12 is a cross-sectional view describing a configuration of a diaphragm pump of the reagent preparing device according to the first embodiment shown in FIG. 1.
Figure 13:
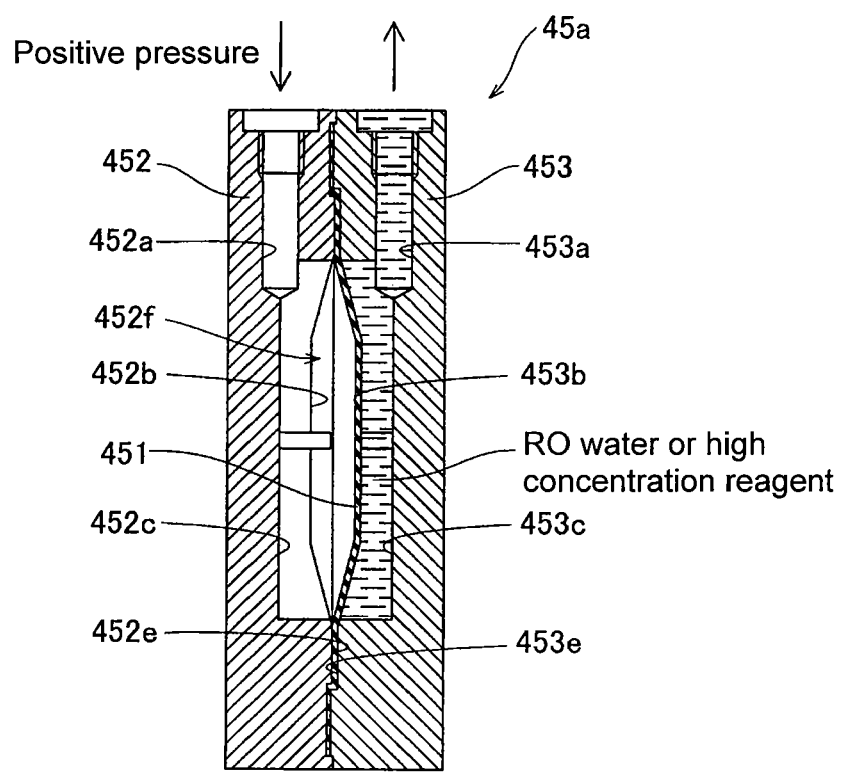
FIG. 13 is a cross-sectional view describing a configuration of a diaphragm pump of the reagent preparing device according to the first embodiment shown in FIG. 1.

The flow port 452a is connected to the negative pressure source 61 and the positive pressure source 62. The flow port 453a is connected to the flow path 302 connected to the RO water chamber 42 and the flow path 301 for transferring the liquid to the first diluting chamber 43 (second diluting chamber 44). The diaphragm pump 45a is configured such that the membrane body 451 closely attaches to the inner wall 452b, as shown in FIG. 12, when the negative pressure is supplied to the chamber portion 452f by the negative pressure source 61 connected to the flow port 452a. The volume of the chamber portion 453f partitioned by the membrane body 451 is thereby enlarged, and the liquid (RO water, high concentration reagent, or mixed solution of RO water and high concentration reagent) flows into the chamber portion 453f through the flow port 453a. The diaphragm pump 45a is configured such that the membrane body 451 closely attaches to the inner wall 453b, as shown in FIG. 13, when the positive pressure is supplied to the chamber portion 452f by the positive pressure source 62 connected to the flow port 452a. The volume of the chamber portion 453f partitioned by the membrane body 451 then becomes substantially zero, and the liquid in the chamber portion 453f flows out (is pushed out) through the flow part 453a. The diaphragm pump 45a is configured so that the liquid amount that flows out in this case is about 6.0 mL. The supplying operation of the liquid (RO water and high concentration reagent) by the diaphragm pumps 45a and 45b includes two steps of flow-in of the liquid and the flow-out of the liquid. When a predetermined flow path is selected from the flow paths 300 to 304 in the respective step, the high concentration reagent or the RO water is flowed in from the high concentration reagent chamber 41 or the RO water chamber 42, quantified about every 12 mL (about 6.0 mL×2) to the first diluting chamber 43 or the second diluting chamber 44, and supplied over plural times. The high concentration chamber 41, the RO water chamber 42, the diaphragm pumps 45a and 45b, the pneumatic unit 6, the flow paths 300 to 304, and the electromagnetic valves 200 to 210 and 213 to 216 configure the liquid quantifying unit 50 (see FIG. 6) of the reagent preparing device 4. The supplying operation of the RO water and the high concentration reagent by the diaphragm pumps 45a and 45b will be described in detail later.

As shown in FIG. 6, the stirring chamber 46 is configured to accommodate about 300 mL of liquid, and is provided to accommodate and stir the liquid (mixed solution of high concentration reagent and RO water) transferred from the first diluting chamber 43 (second diluting chamber 44). Specifically, the stirring chamber 46 includes a bent pipe 461, and is configured so that the liquid (mixed solution of high concentration reagent and RO water) supplied from the first diluting chamber 43 (second diluting chamber 44) flows into the stirring chamber 46 along the inner wall surface of the stirring chamber 46 by passing the pipe 461. The liquid (mixed solution of high concentration reagent and RO water) supplied from the first diluting chamber 43 (second diluting chamber 44) thus flows along the inner wall surface of the stirring chamber 46, whereby convection occurs and the high concentration reagent and the RO water are easily stirred. The high concentration reagent and the RO water are stirred to a certain extent in the first diluting chamber 43 (second diluting 44) and in the flow path from the first diluting chamber 43 (second diluting chamber 44) to the stirring chamber 46, but the solution is more reliably stirred by configuring the stirring chamber 46 in the above manner.

The stirring chamber 46 includes a float switch 105 for detecting that the remaining amount of the liquid (mixed solution of high concentration reagent and RO water) accommodated in the chamber has reached a predetermined amount. The float switch 105 is configured such that the float portion moves up and down according to the liquid amount (liquid level) in the stirring chamber 46. Each unit is controlled by the control unit 49 such that about 300 mL of mixed solution (total amount of mixed solution accommodated in the chamber) is supplied from either the first diluting chamber 43 or the second diluting chamber 44 to the stirring chamber 46 when the float portion of the float switch 105 reaches the lower limit and the interior of the chamber becomes empty. When the mixed solution supplied from either the first diluting chamber 43 or the second diluting chamber 44 and stirred is discharged from the stirring chamber 46, about 300 mL of mixed solution is then supplied from the other one of the first diluting chamber 43 or the second diluting chamber 44 to the stirring chamber 46. The supplying operation of the mixed solution from the first diluting chamber 43 and the second diluting chamber 44 is alternately performed. In the first embodiment, each unit is controlled by the control unit 49 so that while one of the diaphragm pumps 45a and 45b is performing the supplying operation of the RO water and the high concentration reagent to one diluting chamber (e.g., first diluting chamber 43), the supplying operation of the mixed solution accommodated in the other diluting chamber (e.g., second diluting chamber 44) to the stirring chamber 46 can be performed. The stirring chamber 46 is connected to the negative pressure source 61 through the electromagnetic valve 217, and connected to the positive pressure source 62 through the electromagnetic valve 218.

The supplying operation of the mixed solution from the first diluting chamber 43 to the stirring chamber 46 is carried out by opening the electromagnetic valve 211 of the first diluting chamber 43 and the electromagnetic valve 217 of the negative pressure source 61, and closing the electromagnetic valve 212 of the second diluting chamber 44 and the electromagnetic valve 218 of the positive pressure source 62 so that negative pressure force is supplied to the stirring chamber 46 and the mixed solution (total amount) flows in from the first diluting chamber 43. The supplying operation of the mixed solution from the second diluting chamber 44 to the stirring chamber 46 is carried out by opening the electromagnetic valve 212 of the second diluting chamber 44 and the electromagnetic valve 217 of the negative pressure source 61, and closing the electromagnetic valve 211 of the first diluting chamber 43 and the electromagnetic valve 218 of the positive pressure source 62 so that negative pressure force is supplied to the stirring chamber 46 and the mixed solution (total amount) flows in from the second diluting chamber 44.

The supply chamber 47 is arranged to store a predetermined amount of reagent waiting to be supplied to the measurement section 2. The supply chamber 47 is configured to accommodate a mixed solution of greater than or equal to a total amount of the maximum liquid amount (about 300 mL) of the mixed solution accommodated in the first diluting chamber 43 and the second diluting chamber 44 respectively. In the first embodiment, the supply chamber 47 has a capacity (e.g., about 800 mL) of accommodating the maximum liquid amount or about 600 mL of reagent (stirred mixed solution having predetermined concentration). The supply chamber 47 includes a float switch 106 for detecting that the remaining amount of reagent stored in the chamber has reached about 300 mL. The supply chamber 47 also includes a float switch 107 for detecting that the remaining amount of reagent stored in the supply chamber 47 is substantially zero. The float switch 106 (107) is configured such that the float portion moves up and down according to the liquid amount (liquid level) in the supply chamber 47. The float portion of the float switch 106 is configured to be movable from the vicinity of the upper end in the height direction of the supply chamber 47 to the intermediate position. Each unit is controlled by the control unit 49 so that about 300 mL of reagent of the desired concentration is supplied from the stirring chamber 46 to the supply chamber 47 when the float portion of the float switch 106 reaches the intermediate position in the height direction of the supply chamber 47 (lower limit position in the movable range of the float portion of the float switch 106). The reagent of desired concentration of greater than or equal to about 300 mL and less than or equal to about 600 mL is stored in the supply chamber 47 on a constant basis. Thus the reagent can be constantly supplied to the measurement section 2 by storing a predetermined amount of reagent in the supply chamber 47. The degradation of the reagent is suppressed even if the reagent is stored in the supply chamber 47 since the reagent contains antiseptic.

The float portion of the float switch 107 is configured to be movable to the vicinity of the bottom of the supply chamber 47. The supply of reagent to the measurement section 2 is stopped when detected that the remaining amount of reagent accommodated in the chamber is substantially zero by the float switch 107. Therefore, the air bubbles are prevented from mixing to the reagent to be supplied to the measurement section 2 while continuing the supply of reagent to the measurement section 2 as much as possible even if the reagent is not transferred to the supply chamber 47 for some reasons.

The supply chamber 47 is connected to the stirring chamber 46 through the electromagnetic valve 219. The supply chamber 47 is configured so that the reagent in the chamber can be discarded at the time of maintenance and the like by opening the electromagnetic valve 220. The supply chamber 47 is configured so as to be opened to atmosphere on a constant basis. The supply chamber 47 is connected to the measurement section 2 through the filter 471. The filter 471 is arranged to prevent impurities from mixing in the reagent to be supplied to the measurement section 2.

A conductivity sensor 402 for measuring the electrical conductivity of the reagent is arranged between the stirring chamber 46 and the supply chamber 47. The conductivity sensor 402 includes a temperature sensor 403 for measuring the temperature of the reagent at the position where the conductivity sensor 402 is arranged. A discard flow path is connected between the conductivity sensor 402 and the electromagnetic valve 219 through the electromagnetic valve 221.

The RO water producing unit 48 is configured so that the RO water serving as the diluting liquid for diluting the high concentration reagent can be produced using tap water. The RO water producing unit 48 includes an RO water storage tank 48a, an RO membrane 48b, and a filter 48c for protecting the RO membrane 48b by removing impurities contained in the tap water. Furthermore, the RO water producing unit 48 includes a high pressure pump 48d for applying high pressure to the water passed through the filter 48c so that water molecules transmit through the RO membrane 48b, and an electromagnetic valve 222 for controlling the supply of tap water.

The RO water storage tank 48a is arranged to store the RO water transmitted through the RO film 48b. The RO water storage tank 48a includes a float switch 108 for detecting that a predetermined amount of RO water is stored. The RO water storage tank 48a includes a conductivity sensor 404 for measuring the electrical conductivity of the RO water in the RO water storage tank 48a. The conductivity sensor 404 includes a temperature sensor 405 for measuring the temperature of the RO water. The speed the RO water is supplied from the RO water producing unit 48 to the RO water storage tank 48a, that is, the production speed of the RO water by the RO water producing unit 48 is greater than or equal to about 20 L/hour and smaller than or equal to about 50 L/hour.

Figure 14:
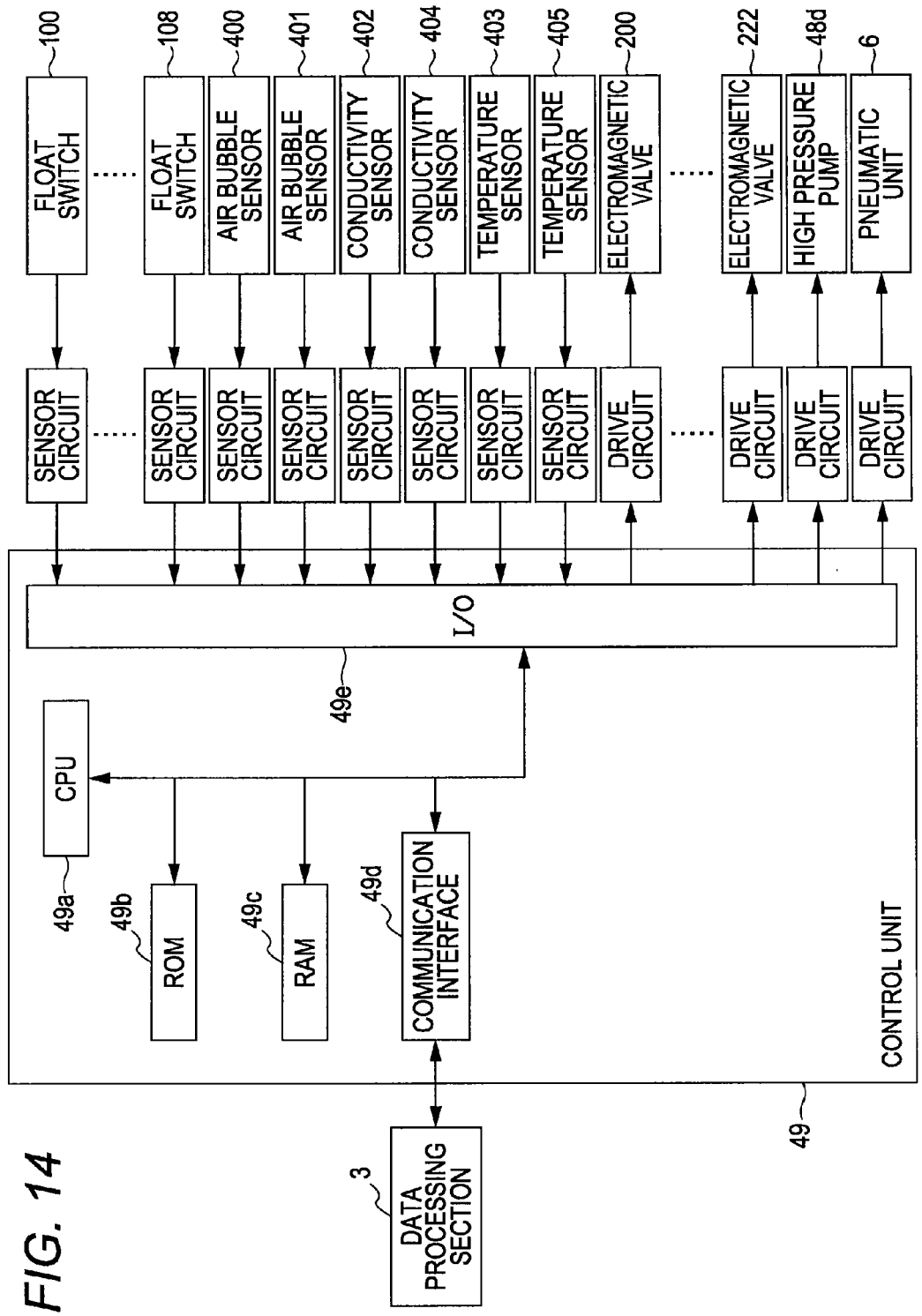
FIG. 14 is a block diagram for describing a control unit of the reagent preparing device according to the first embodiment of the present invention.

As shown in FIG. 14, the control unit 49 includes a CPU 49a, a ROM 49b, a RAM 49c, a communication interface 49d connected to the data processing section 3, and an I/O (Input/Output) portion 49e connected to each unit in the reagent preparing device 4 through each circuit.

The CPU 49a can execute computer programs stored in the ROM 49b and the computer programs loaded in the RAM 49c. The CPU 49a is configured to use the RAM 49c as a work region when executing the computer programs.

A general formula for obtaining a target value of the electrical conductivity of the reagent is expressed with the following equation (1).

$$Z_0 = \{X + (A-1)Y\}/A \quad (1)$$

In the equation (1), $Z_0$ is, at 25° C., the target value (ms/cm) of the electrical conductivity of the reagent in which the high concentration reagent and the RO water are mixed and stirred, X is the electrical conductivity (ms/cm) of the high concentration reagent at 25° C., Y is the electrical conductivity (ms/cm) of the RO water at 25° C., and A is the diluting magnification (known) (25 times in the first embodiment). Here, X is a value unique to the high concentration reagent, and is a known value obtained through experiments and the like in advance.

The correction formula for taking into consideration the temperature of the RO water obtained by the temperature sensor 405 and the temperature of the reagent obtained by the temperature sensor 403 is expressed with the following equation (2).

$$Z = [\{X+(A-1)Y\}/A] \times \{1+\alpha1(T2-25)\} = [[X+(A-1)Y1/\{1+\alpha0(T1-25)\}]/A] \times \{1+\alpha1(T2-25)\} \quad (2)$$

In the equation (2), Z is, at T2° C., the target value (ms/cm) of the electrical conductivity of the reagent in which the high concentration reagent and the RO water are mixed and stirred, Y1 is the electrical conductivity of the RO water at T1° C., T1 is the temperature of the RO water (° C.), T2 is the temperature (° C.) of the reagent in which the high concentration reagent and the RO water are mixed and stirred, $\alpha0$ is the temperature coefficient compared with the electrical conductivity of the RO water at 25° C., and $\alpha1$ is the temperature coefficient compared with the electrical conductivity of the reagent in which the high concentration reagent and the RO water are mixed and stirred, at 25° C. The temperature coefficients $\alpha0$ and $\alpha1$ differ depending on the type and concentration of the liquid, but are 0.02 for simplification in JIS (Japanese Industrial Standards).

The CPU 49a is configured to calculate the target value Z from the equation (2). Therefore, the CPU 49a determines the target value based on the desired diluting magnification A (known), the detection value Y1 of the electrical conductivity of the RO water, the measurement value T1 of the temperature of the RO water, the measurement value T2 of the temperature of the mixed and stirred reagent, and the electrical conductivity X (known) of the high concentration reagent.

The communication interface 49d is configured to transmit error information to the data processing section 3 so that the user can check the error that occurred in the reagent preparing device 4. The error information includes information for urging replacement of the high concentration reagent tank 5, information notifying that the RO water is no longer supplied, and information notifying the abnormality of the negative pressure source 61 and the positive pressure source 62. An error notification is displayed on the display unit 32 of the data processing section 3 based on the error information.

As shown in FIG. 14, the I/O portion 49e is configured so that signals are input from the float switches 100 to 108, the air bubble sensors 400, 401, the conductivity sensors 402, 404, and the temperature sensors 403, 405 through each sensor circuit. The I/O portion 49e is configured to output signals to each drive circuit to control the drive of the electromagnetic valves 200 to 222, the high pressure pump 48d, and the pneumatic unit 6 through each drive circuit.

The reagent preparation processing operation (liquid supplying operation) of the reagent preparing device 4 according to the first embodiment of the present invention will now be described with reference to FIGS. 6, 15, and 16.

The reagent preparation processing operation starts when the user instructs the activation of the device from the data processing section 3, that is, when the reagent preparing device 4 receives the activation signal from the data processing section 3. When the reagent preparation processing operation starts, initialization of the computer program stored in the ROM 49b is performed by the CPU 49a in step S1 of FIG. 15. In step S2, the CPU 49a determines whether or not the reagent preparing device 4 is normally shut down at the end of the previous operation. Specifically, determination is made based on a flag set to ON when normally shut down, as hereinafter described. The process proceeds to step S6 if normally shut down, and the process proceeds to step S3 if not normally shut down.

In step S3, the liquid in the chambers 42, 43, 44 and 46 other than the high concentration reagent chamber 41 and the supply chamber 47 are all discarded. Specifically, the electromagnetic valve 205 is opened by the CPU 49a to discard the RO water in the RO water chamber 42. The electromagnetic valve 221 is opened by the CPU 49a to discharge the mixed solution in the stirring chamber 46 to the discard flow path. Furthermore, the electromagnetic valves 211 and 217 are opened by the CPU 49a to transfer the mixed solution in the first diluting chamber 43 to the stirring chamber 46 with the negative pressure force, and thereafter, the mixed solution is discarded from the stirring chamber 46 through the operations described above. The mixed solution of the second diluting chamber 44 is also transferred to the stirring chamber 46 with the negative pressure force by opening the electromagnetic valves 212 and 217 by the CPU 49a.

Therefore, the RO water having a possibility of being accumulated for a long time is prevented from being used in the reagent preparation, and the reagent of unknown diluting magnification is prevented from being prepared by discarding all liquids in the chambers 42, 43, 44, and 46 other than the high concentration reagent chamber 41 and the supply chamber 47 in step S3.

The quality of the high concentration reagent of the high concentration reagent chamber 41 does not degrade with the accumulated time of about one month since high concentration reagent of the high concentration reagent chamber 41 contains antiseptic, and thus the high concentration reagent in the high concentration regent chamber 41 does not need to be discarded. Only the reagent diluted to the desired concentration is stored in the supply chamber 47, as hereinafter described, and the antiseptic contained in the high concentration reagent is mixed therein, and thus such liquid does not need to be discarded as the quality of the stored reagent does not have problems.

Thereafter, in step S4, the flow path, the RO water chamber 42, the first diluting chamber 43 (second diluting chamber 44) and the stirring chamber 46 are cleaned. Specifically, the RO water is transferred to the stirring chamber 46 through the first diluting chamber 43 by controlling each unit by means of the CPU 49a after the RO water newly produced in the RO water producing unit 48 is supplied to the RO water chamber 42. The RO water in the stirring chamber 46 is then discarded. Furthermore, the newly produced RO water is supplied to the second diluting chamber 44 while the RO water is being transferred from the first diluting chamber 43 to the stirring chamber 46. Thereafter, the RO water is similarly transferred to the stirring chamber 46, and the RO water is discarded. The interior of the flow path, the RO water chamber 42, the first diluting chamber 43 (second diluting chamber r44), and the stirring chamber 46 are cleaned with the newly produced RO water through the series of operations described above.

In step S5, the reagent is prepared in the stirring chamber 46 through the operation similar to the operation of preparing the reagent of desired concentration, and all prepared reagent are discarded. Thus, the reagent is suppressed from being prepared to the concentration other than the desired concentration since cleaning is carried out with the reagent of the desired concentration in addition to the cleaning by the RO water.

In step S6, the RO water production process is performed in the RO water producing unit 48. The RO water production processing operation in step S6 of the reagent preparation processing operation shown in FIG. 15 will now be described with reference to FIGS. 6 and 17.

Figure 17:
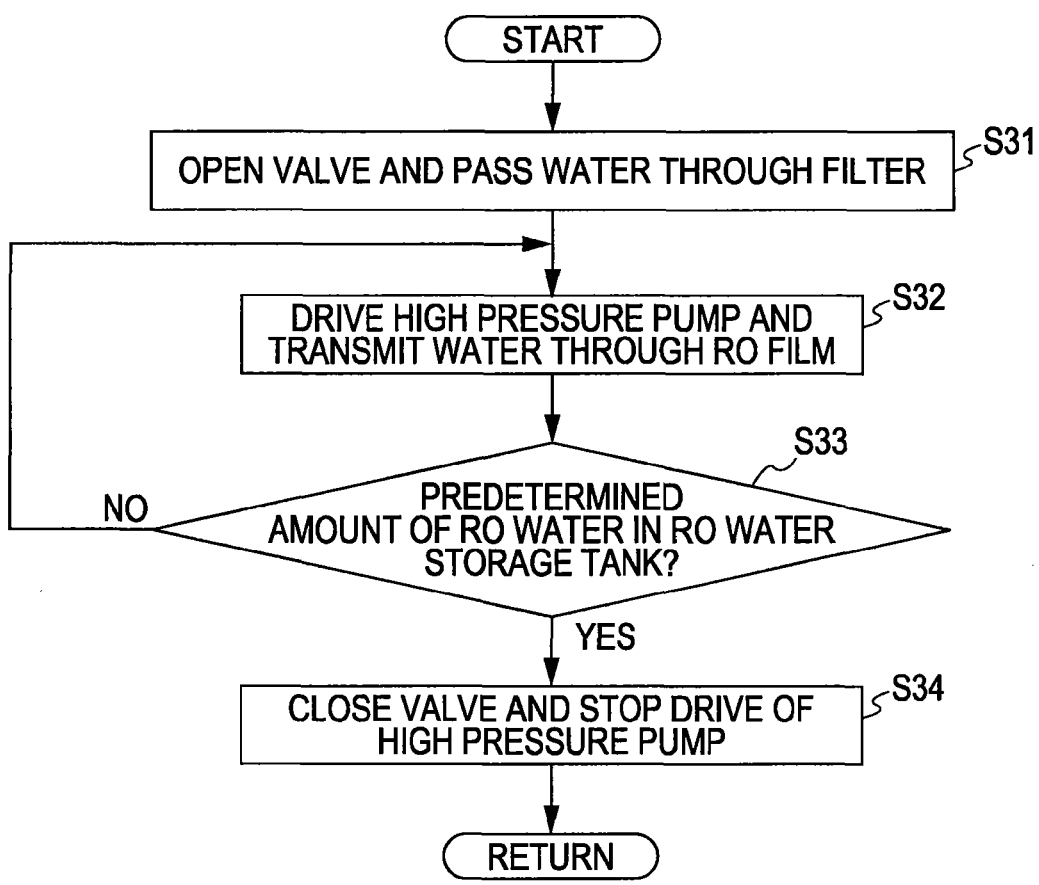
FIG. 17 is a flowchart describing the RO water production processing operation in step S6 of the reagent preparation processing operation shown in FIG. 15.

First, in step S31 of FIG. 17, the electromagnetic valve 222 shown in FIG. 6 is opened by the CPU 49a and the tap water is passed through the filter 48c. In step S32, the high pressure pump 48d is driven by the CPU 49a, and the water passed through the filter 48c is transmitted through the RO film 48b by the high pressure. In step S33, whether or not a predetermined amount of RO water is accommodated in the RO water storage tank 48a is determined based on the detection result of the float switch 108. If the RO water is not the predetermined amount, the process returns to step S32, and the RO water is continuously supplied to the RO water storage tank 48a. If the RO water is the predetermined amount, the electromagnetic valve 222 is closed and the drive of the high pressure pump 48d is stopped in step S34 and the operation is terminated.

Figure 15:
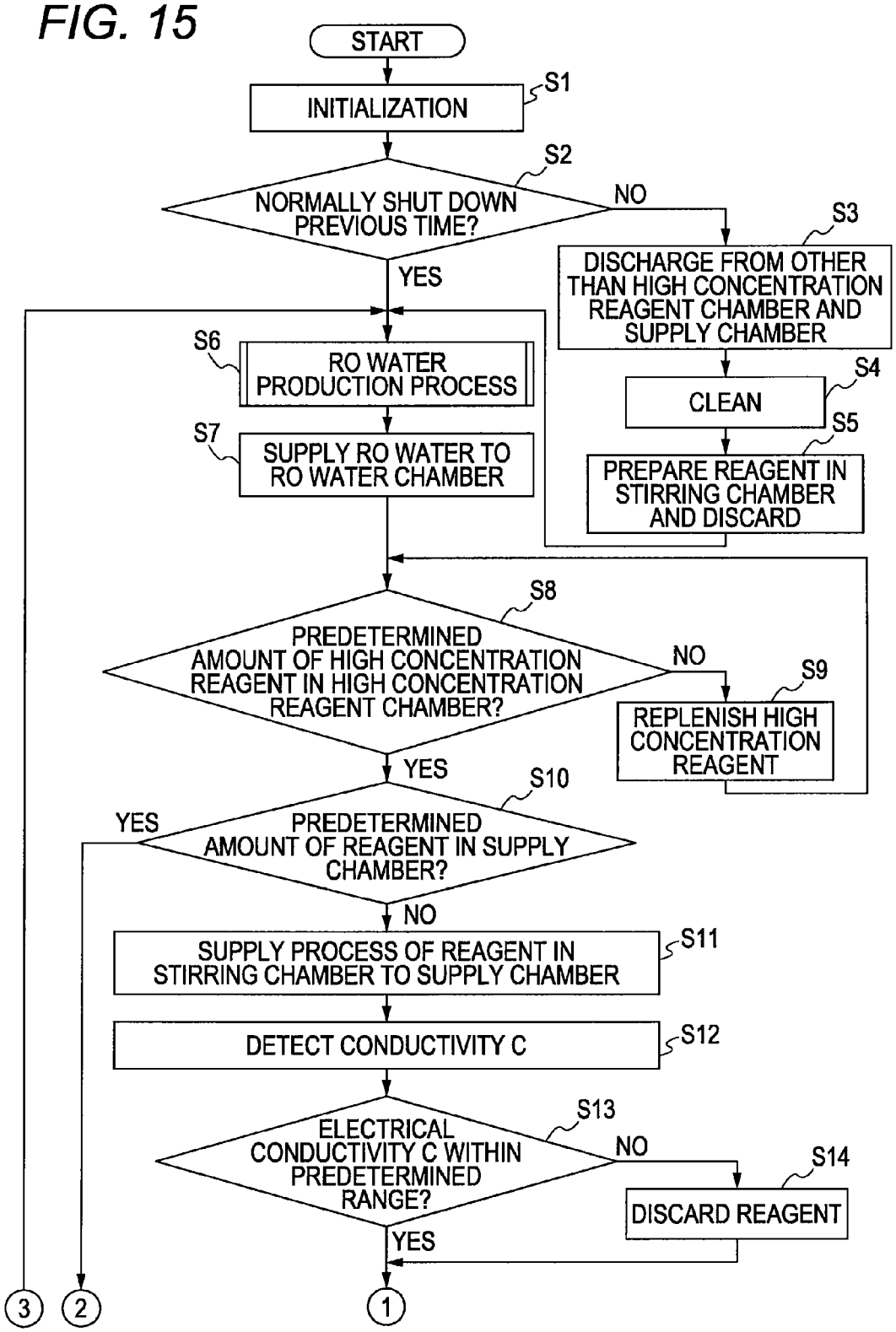
FIG. 15 is a flowchart describing the reagent preparation processing operation of the reagent preparing device according to the first embodiment of the present invention.

After the RO water production processing operation of step S6 of FIG. 15 is terminated, the RO water is supplied to the RO water chamber 42 in step S7. In step S8, whether or not a predetermined amount of high concentration reagent is accommodated in the high concentration reagent chamber 41 is determined based on the detection result of the float switch 100 by the CPU 49a. If the predetermined amount of high concentration reagent is not stored, the high concentration reagent is replenished to the high concentration reagent chamber 41 from the high concentration reagent tank 5 in step S9. Specifically, the electromagnetic valves 200 and 201 are opened with the electromagnetic valves 202 and 203 closed by the CPU 49a, so that the high concentration reagent is supplied to the high concentration reagent chamber 41 with the negative pressure force.

If the predetermined amount of high concentration reagent is accommodated in the high concentration reagent chamber 41, whether or not the predetermined amount of reagent is stored in the supply chamber 47 is determined by the CPU 49a. In other words, whether or not the reagent of greater than or equal to about 300 mL and less than or equal to about 600 mL is stored in the supply chamber 47 is determined based on the detection result of the float switch 106. The process proceeds to step S20 (see FIG. 16) if the predetermined amount of reagent is stored.

If the predetermined amount of reagent is not stored, the electromagnetic valves 218 and 219 are opened after the electromagnetic valves 211 (212) and 217 are closed, and the reagent is transferred from the stirring chamber 46 to the supply chamber 47 in step S11. In step S12, the electrical conductivity C is measured by the conductivity sensor 402 and the temperature T2 of the reagent is measured by the temperature sensor 403. In step S13, whether or not the electrical conductivity C is within a predetermined range is determined by the CPU 49a. Specifically, whether or not the measured electrical conductivity C is within the predetermined range is determined with respect to the target value Z of the electrical conductivity at the diluting magnification of 25 times calculated by equation (2). If the electrical conductivity C is not within the predetermined range, the electromagnetic valve 219 is closed and the electromagnetic valve 221 is opened, and the reagent in which the electrical conductivity C is not within the predetermined range is discarded through the discard flow path in step S14. Only the reagent diluted at satisfactory accuracy thus can be stored in the supply chamber 47.

Figure 16:
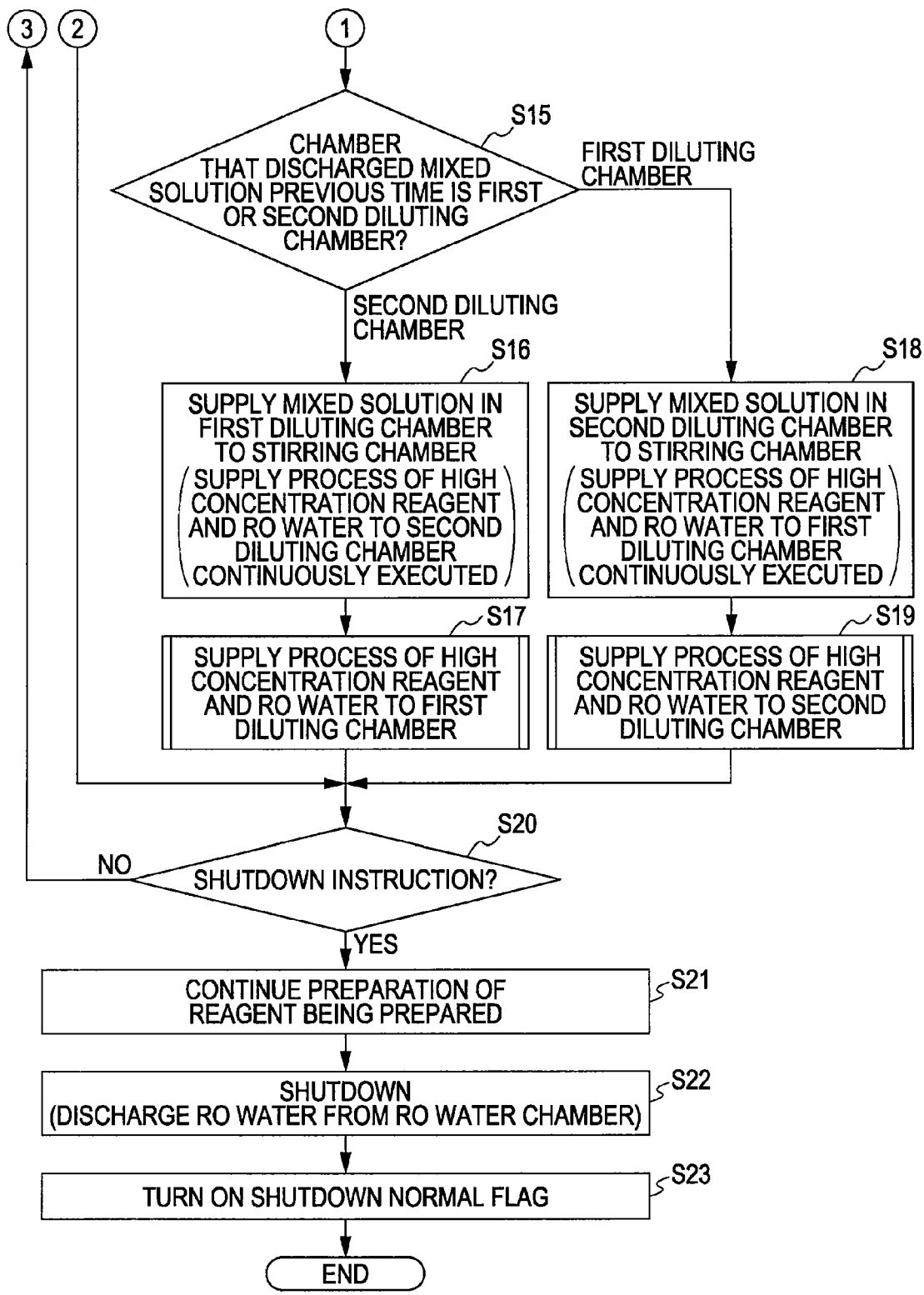
FIG. 16 is a flowchart describing the reagent preparation processing operation of the reagent preparing device according to the first embodiment of the present invention.

When detected by the float switch 105 that the reagent in the stirring chamber 46 is empty as a result of the reagent being supplied from the stirring chamber 46 to the supply chamber 47 or being discarded, whether the chamber that discharged the mixed solution the previous time is the first diluting chamber 43 or the second diluting chamber 44 is determined by the CPU 49a in step S15 as shown in FIG. 16. The control unit 49 stores whether the chamber that discharged the mixed solution the previous time is the first diluting chamber 43 or the second diluting chamber 44, and updates to the most recent information by the CPU 49a every time the mixed solution is discharged from the first diluting chamber 43 or the second diluting chamber 44.

If determined that the chamber that discharged the mixed solution the previous time is the second diluting chamber 44 in step S15, the mixed solution accommodated in the first diluting chamber 43 is supplied to the stirring chamber 46 in step S16. Specifically, the electromagnetic valves 211 and 217 are opened with the electromagnetic valves 212 and 218 closed by the CPU 49a to supply the mixed solution in the first diluting chamber 43 to the stirring chamber 46 with the negative pressure force. About 300 mL of mixed solution accommodated in the first diluting chamber 43 is thus all supplied to the stirring chamber 46. The mixed solution to be supplied flows along the inner walls of the stirring chamber 46 by the pipe 461 arranged in the stirring chamber 46 so as to be stirred in the stirring chamber 46. When the reagent is continuously used by the measurement section 2, the supplying operation of the high concentration reagent and the RO water to the second diluting chamber (step S19), to be described later, is sometimes continued while the process of step S16 (supplying operation) is being executed.

When the total amount of mixed solution accommodated in the first diluting chamber 43 is supplied to the stirring chamber 46, the high concentration reagent and the RO water are supplied to the emptied first diluting chamber 43 in step S17. Specifically, the supplying operation of the high concentration reagent and the RO water to the first diluting chamber 43 by the diaphragm pump 45a (45b) is performed by the CPU 49a based on the detection result of the float switch 103. The details on the supplying operation of the high concentration reagent and the RO water will be described later.

If determined that the chamber that discharged the mixed solution the previous time is the first diluting chamber 43 in step S15, the process proceeds to step S18, and the mixed solution accommodated in the second diluting chamber 44 is supplied to the stirring chamber 46. Specifically, the electromagnetic valves 212 and 217 are opened with the electromagnetic valves 211 and 218 closed by the CPU 49a to supply the mixed solution in the second diluting chamber 44 to the stirring chamber 46 with the negative pressure force. The total amount of about 300 mL of mixed solution accommodated in the second diluting chamber 44 is then supplied to the stirring chamber 46. If the reagent is continuously used by the measurement section 2, the supplying operation (step S17) of the high concentration reagent and the RO water to the first diluting chamber may be continued while the process of step S18 (supplying operation) is being executed.

When the total amount of mixed solution accommodated in the second diluting chamber 44 is supplied to the stirring chamber 46, the high concentration reagent and the RO water are supplied to the emptied second diluting chamber 44 in step S19. Specifically, the supplying operation of the high concentration reagent and the RO water to the second diluting chamber 44 by the diaphragm pump 45a (45b) is performed by the CPU 49a based on the detection result of the float switch 104.

The supply processing operation of the high concentration reagent and the RO water in steps S17 and S19 of the reagent preparation processing operation shown in FIG. 16 will be described with reference to FIGS. 6, 12, 13, and 18. The supply processing operation of the high concentration reagent and the RO water in step S17 and the supply processing operation of the high concentration reagent and the RO water in step S19 are substantially the same process differing only in the supplying destination of the high concentration reagent and the RO water. Specifically, the supplying destination is the first diluting chamber 43 in step S17, and the supplying destination is the second diluting chamber 44 in step S19.

First, in the initial state (state immediately before reagent preparation process) of the reagent preparing device 4, the flow paths 301 to 304 shown in FIG. 6 are substantially filled with RO water and the flow path 300 is substantially filled with high concentration reagent. The flow path 300 and the flow path 301 are directly connected, but the high concentration reagent in the flow path 300 is difficult to mix with the RO water in the flow path 301 since the inner diameter of the flow path 301 is about 4.0 mm and the inner diameter of the flow path 300 (300a) is small or about 1.8 mm. The flow path 300a between the electromagnetic valve 203 and the flow path 301 is set such that the inner diameter is about 1.8 mm and the length is small or about 15 mm, and thus the amount of high concentration reagent in the flow path 300a is very small.

Figure 18:
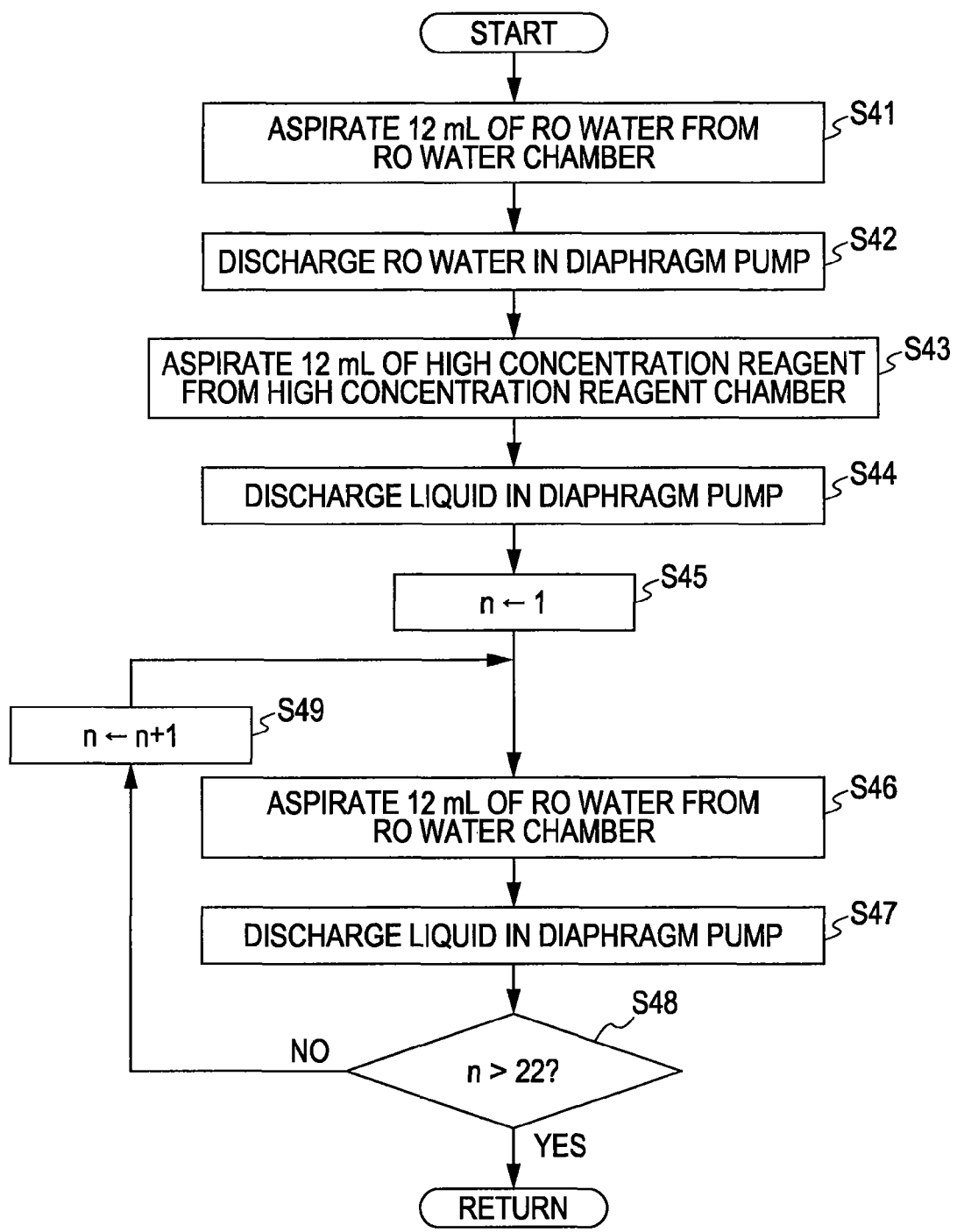
FIG. 18 is a flowchart describing the supply processing operation of the high concentration reagent and the RO water in steps S17 and S19 of the reagent preparation processing operation shown in FIG. 16.

In step S41 of FIG. 18, about 12.0 mL (about 6.0 mL in each diaphragm pump) of RO water is aspirated from the RO water chamber 42 by the diaphragm pumps 45a and 45b. Specifically, the electromagnetic valves 213 (215) and 208 are opened by the CPU 49a, so that the negative pressure is supplied to the chamber portion 452f (see FIG. 9) and the film body 451 closely attaches to the inner wall portion 452b, as shown in FIG. 12. The RO water flows into the chamber portion 453f through the flow path 302 with the enlargement of the capacity of the chamber portion 453f.

In step S42, the electromagnetic valves 214 (216) and the electromagnetic valve 209 (step S17) or the electromagnetic valve 210 (step S19) are opened after the electromagnetic valves 213 (215) and 208 are closed, so that positive pressure is supplied to the chamber portion 452f and the film body 451 closely attaches to the inner wall portion 453b as shown in FIG. 13. The RO water is discharged from the chamber portion 453f (see FIG. 12) with the enlargement of the capacity of the chamber portion 452f. Thus, in step S17, about 12.0 mL (about 6.0 mL in each diaphragm pump) of RO water is supplied to the first diluting chamber 43 through the flow paths 301 and 303. In step S19, about 12.0 mL (about 6.0 mL in each diaphragm pump) of RO water is supplied to the second diluting chamber 44 through the flow paths 301 and 304.

Thereafter, in step S43, about 12.0 mL (about 6.0 mL in each diaphragm pump) of high concentration reagent is aspirated from the high concentration reagent chamber 41 by the diaphragm pumps 45a and 45b. Specifically, the electromagnetic valves 202, 203, and 213 (215) are opened by the CPU 49a after the electromagnetic valves 214 (216) and 209 (210) are closed, so that the negative pressure is supplied to the chamber portion 452f (see FIG. 13), as shown in FIG. 12. The high concentration reagent is aspirated to the chamber portion 453f through the flow paths 300 and 301 with the enlargement of the capacity of the chamber portion 453*f*. Specifically, about 12.0 mL of high concentration reagent flowed out from the high concentration reagent chamber 41 mixes with the RO water remaining in the flow path 301, and the mixed solution of the RO water and the high concentration reagent is aspirated to the chamber portion 453*f*. The mixed solution of the RO water and the high concentration reagent is filled in the flow path 301 in this case. In other words, about 12.0 mL of high concentration reagent flowed out from the high concentration reagent chamber 41 exists in a region combining the chamber portion 453*f* and the flow path 301 in this state. The high concentration reagent also exists in the flow path 300*a*, but can be substantially ignored as the amount of high concentration reagent existing in the flow path 300*a* is very small. Furthermore, at the time of aspirating the high concentration reagent after the second reagent preparation processing operation, the high concentration reagents remaining in the flow path 300*a* from the previous reagent preparation processing operation is pushed out to the flow path 301 side, and thus about 12.0 mL of high concentration reagent more accurately exists in the region combining the chamber portion 453*f* and the flow path 301.

In step S44, the electromagnetic valve 214 (216) and the electromagnetic valve 209 (step S17) or the electromagnetic valve 210 (step S19) are opened after the electromagnetic valves 202, 203, and 213 (215) are closed, so that positive pressure is supplied to the chamber portion 452*f* thereby enlarging the capacity of the chamber portion 452*f*, and the mixed solution of RO water and high concentration reagent is discharged from the chamber portion 453*f* (see FIG. 12), as shown in FIG. 13. Thus, the mixed solution of RO water and high concentration reagent is supplied to the first diluting chamber 43 through the flow paths 301 and 303 in step S17. In step S19, the mixed solution of RO water and high concentration reagent is supplied to the second diluting chamber 44 through the flow paths 301 and 304. In this case, a few mL of high concentration reagent remains mixed with the RO water in the flow path 301 and the flow path 303 (step S17) or the flow path 304 (step S19).

In step S45, n=1 is set by the CPU 49*a*. Here, n is the number of discharging of the RO water by the diaphragm pumps 45*a* and 45*b*, and is defined with a real number starting from 1. In step S46, about 12.0 mL of RO water is aspirated from the RO water chamber 42 by the diaphragm pumps 45*a* and 45*b*, similar to step S41. Similar to step S42, in step S47, the RO water is discharged from the chamber portion 453*f* of the diaphragm pumps 45*a* and 45*b*. Thus, the high concentration reagent remaining in the flow paths 301 and 303 is supplied to the first diluting chamber 43 with the RO water in step S17. In step S19, the high concentration reagent remaining in the flow paths 301 and 304 is supplied to the second diluting chamber 44 with the RO water.

Thereafter, in step S48, whether or not n is greater than 22 is determined by the CPU 49*a*. If n is not greater than 22, n=n+1 is set in step S49, and the operations of steps S46 to S49 are repeated until n is greater than 22. In other words, the operations of steps S46 to S49 are repeated until the aspiration and discharge operation of the RO water are performed 24 times with respect to one aspiration and discharge operation of the high concentration reagent by the diaphragm pumps 45*a* and 45*b*. The operation is terminated when n is greater than 22. Thus, about 12.0 mL×24 times=about 288 mL of RO water and about 12.0 mL×1 time=about 12 mL of high concentration reagent, or the mixed solution of about 288 mL+about 12 mL=about 300 mL is supplied to the first diluting chamber 43 (step S17) or the second diluting chamber 44 (step S19). After the aspiration and discharge operation of the high concentration reagent by the diaphragm pumps 45*a* and 45*b*, the aspiration and discharge operation of the RO Water is performed 23 times, and thus the high concentration reagent remaining in the flow paths 301 and the flow path 303 (step S17) or the flow path 304 (step S19) are all transferred to the first diluting chamber 43 or the second diluting chamber 44. As a result, only the RO water exists in the flow path 301 and the flow path 303 or the flow path 304. Thus, the supplying operation of the high concentration reagent and the RO water to the first diluting chamber 43 and the second diluting chamber 44 by the diaphragm pumps 45*a* and 45*b* is performed by the aspirating and discharging operation of a total to 25 times. The aspirating and discharging operation of the liquid in steps S41 to S44, S46, and S47 is executed by simultaneously operating the diaphragm pumps 45*a* and 45*b*.

As shown in FIG. 16, in step S20, the presence of shutdown instruction from the user is determined by the CPU 49*a*, and the process proceeds to step S6 if the instruction is not made. Therefore, the processes of steps S6 to S20 are repeated if the shutdown instruction is not made in step S20.

If the shutdown instruction is made, the above operation is continued until the reagent in the middle of the preparation is ultimately transferred to the supply chamber 47 in step S21. Specifically, if a predetermined amount (greater than or equal to about 300 mL and less than or equal to about 600 mL) of reagent is not in the supply chamber 47, the mixed solution diluted to a concentration different from the desired concentration remains in the flow path, the first diluting chamber 43 (second diluting chamber 44), and the stirring chamber 46 when the operation is stopped in the middle of the preparation since the reagent preparation is continued through the operations of steps S11 to S19. Thus, the reagent diluted to a concentration different from the desired concentration is prevented from remaining in the flow path, the first diluting chamber 43 (second diluting chamber 44), and the stirring chamber 46 by continuing the preparing operation in step S21.

In step S22, the shutdown is executed. In this case, the RO water is discharged from the RO water chamber. The RO water is thus prevented from being accumulated in the RO water chamber 42 until the reagent preparing device 4 is activated the next time. Thereafter, in step S23, the flag indicating that the shutdown is normally performed is set to ON, and the reagent preparation processing operation is terminated. The reagent preparation process shown in FIGS. 15 and 16 is continuously executed while the reagent preparing device 4 is operating by the CPU 49*a*. The specimen is measured by the measurement section 2 in parallel to the reagent preparing operation. As shown in FIG. 2, in the measurement section 2, the electromagnetic valve 261 is opened with the electromagnetic valve 262 closed to supply the negative pressure force from the negative pressure source 71 to the measurement sample preparing unit 21, so that the reagent is continuously aspirated (supplied) from the supply chamber 47 of the reagent preparing device 4.

Figure 19:
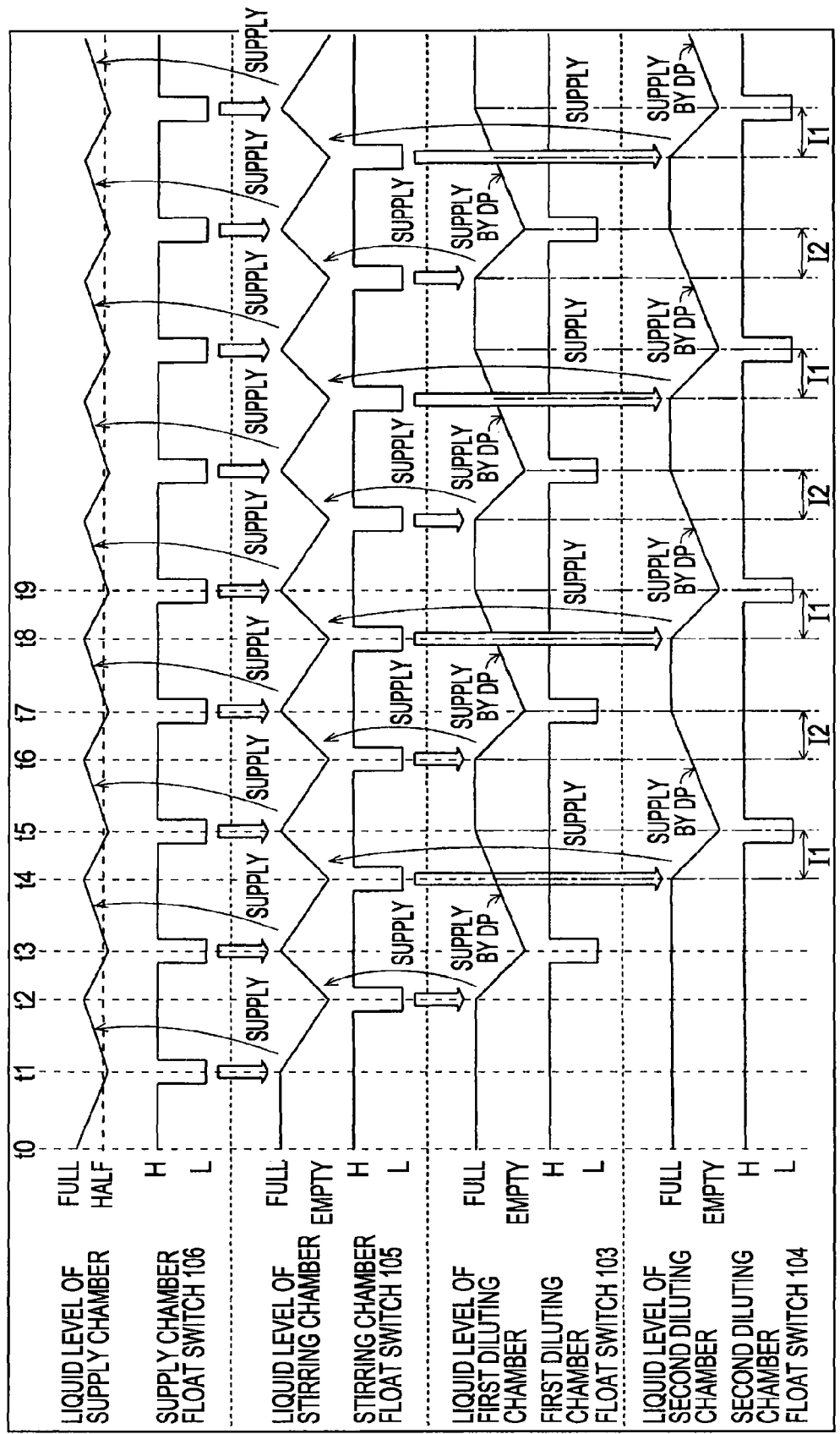
FIG. 19 is a timing chart describing the supplying operation between the chambers of the reagent preparing device according to the first embodiment of the present invention.

One specific operation example of when performing the reagent supplying operation of the reagent preparing device 4 of the blood examination apparatus 1 according to the first embodiment of the present invention will now be described. As shown in FIG. 19, in this operation example, a case in which the measurement is continuously performed by the measurement section 2 so that the usage amount of the reagent by the measurement section 2 (dropped amount of liquid level of the supply chamber 47) is constant and the reagent is continuously used will be described.

As shown in FIG. 19, at timing t0, the reagent in the supply chamber 47, the reagent in the stirring chamber 46, and the mixed solution in the first diluting chamber 43 and the second diluting chamber 44 are in a full state. That is, if normally shutdown in steps S21 to S23 of FIG. 16, the shutdown is executed after the reagent preparing operation is terminated, and hence each chamber is normally in the full state at the time of activation. The measurement of the blood by the measurement section 2 starts from such state, and the aspiration of the reagent (supply of reagent to the measurement section 2) starts from the supply chamber 47 (see FIG. 6) of the reagent preparing device 4 with the generation of the diluted sample, as shown in FIG. 2. Thus, when the measurement by the measurement section 2 starts at timing t0, the liquid level of the reagent in the supply chamber 47 gradually drops from the full-liquid state (about 600 mL).

Thereafter, at timing t1, when the reagent (liquid level) in the supply chamber 47 reduces (drops) to about half the amount (about 300 mL), the supply of reagent from the stirring chamber 46 to the supply chamber 47 starts when the float portion of the float switch 106 (see FIG. 6) reaches the lower limit position (L). In other words, when determined that a predetermined amount (about 300 mL) of reagent is not stored in the supply chamber 47 in step S10 of FIG. 15 by the CPU 49*a*, the supply of about 300 mL of reagent from the stirring chamber 46 to the supply chamber 47 starts (step S11). The liquid level of the supply chamber 47 rises and the liquid level of the stirring chamber 46 lowers from timing t1. When the reagent in the stirring chamber 46 then becomes empty, the termination of the supply of reagent to the supply chamber 47 is detected at timing t2 when the float portion of the float switch 105 (see FIG. 6) reaches the lower limit (L).

At timing t2 when the stirring chamber 46 becomes empty, the supply of reagent from the first diluting chamber 43 to the stirring chamber 46 starts. In other words, the supplying operation of the mixed solution from the first diluting chamber 43 to the stirring chamber 46 starts by the CPU 49*a* (step S16). The liquid level of the stirring chamber 46 then rises and the liquid level of the first diluting chamber 43 lowers from timing t2. In this case, the mixed solution supplied to the stirring chamber 46 is stirred by being supplied to the stirring chamber 46. Thereafter, when the reagent in the first diluting chamber 43 becomes empty, the termination of the supply of reagent to the stirring chamber 46 is detected at timing t3 when the float portion of the float switch 103 (see FIG. 6) reaches the lower limit (L).

At timing t3 when the first diluting chamber 43 becomes empty, the supplying operation of the high concentration reagent and the RO water to the first diluting chamber 43 by the diaphragm pumps (DP) 45*a* and 45*b* ("supply by DP" between timing t3 to t5) starts (step S17 of FIG. 16 starts). The liquid level of the first diluting chamber 43 rises from timing t3. At timing t3, the supply of reagent from the stirring chamber 46 to the supply chamber 47 again starts when the reagent in the supply chamber 47 again reduces to about half the amount (about 300 mL) and the float switch 106 reaches the lower limit position (L). The liquid level of the supply chamber 47 then rises and the liquid level of the stirring chamber 46 lowers from timing t3. Thereafter, when the reagent in the stirring chamber 46 becomes empty, the termination of the supply of reagent to the supply chamber 47 is detected at timing t4 when the float switch 105 reaches the lower limit (L).

At timing t4 when the stirring chamber 46 becomes empty, the supply of reagent from the second diluting chamber 44 to the stirring chamber 46 starts. In other words, the supply operation of the mixed solution from the second diluting chamber 44 to the stirring chamber 46 starts by the CPU 49*a* (step S18). The liquid level of the stirring chamber 46 then rises and the liquid level of the second diluting chamber 44 lowers from timing t4. In parallel thereto, the rise of the liquid level of the first diluting chamber 43 by the supplying operation of the high concentration reagent and the RO water to the first diluting chamber 43 by the diaphragm pumps 45*a* and 45*b* is continued. In the interval I1 between timing t4 and t5, the supplying operation of the mixed solution from the second diluting chamber 44 to the stirring chamber 46 is performed while the high concentration reagent and the RO water are being supplied to the first diluting chamber 43 by the diaphragm pumps 45*a* and 45*b*. Thereafter, the supplying operation of the high concentration reagent and the RO water to the first diluting chamber 43 is completed at timing t5, and the liquid level of the mixed solution in the first diluting chamber 43 becomes full (about 300 mL). When the reagent in the second diluting chamber 44 becomes empty, the termination of the supply of reagent to the stirring chamber 46 is detected at timing t5 when the float switch 104 reaches the lower limit (L).

At timing t5 when the second diluting chamber 44 becomes empty, the supplying operation of the high concentration reagent and the RO water to the second diluting chamber 44 by the diaphragm pumps 45*a* and 45*b* ("supply by DP" between timing t5 to t7) starts (step S19 of FIG. 16 starts). The liquid level of the second diluting chamber 44 rises from timing t5. At timing t5, the supply of reagent from the stirring chamber 46 to the supply chamber 47 again starts when the reagent in the supply chamber 47 again reduces to about half the amount (about 300 mL) and the float switch 106 reaches the lower limit position (L). The liquid level of the supply chamber 47 then rises and the liquid level of the stirring chamber 46 lowers from timing t5. Thereafter, when the reagent in the stirring chamber 46 becomes empty, the termination of the supply of reagent to the supply chamber 47 is detected at timing t6 when the float switch 105 reaches the lower limit (L).

At timing t6 when the stirring chamber 46 becomes empty, the supply of reagent from the first diluting chamber 43 to the stirring chamber 46 starts. In other words, the supply operation of the mixed solution from the first diluting chamber 43 to the stirring chamber 46 starts by the CPU 49*a* (step S16). The liquid level of the stirring chamber 46 then rises and the liquid level of the first diluting chamber 43 lowers from timing t6. In parallel thereto, the rise of the liquid level of the second diluting chamber 44 by the supplying operation of the high concentration reagent and the RO water to the second diluting chamber 44 by the diaphragm pumps 45*a* and 45*b* is continued. In the interval 12 between timing t6 and t7, the supplying operation of the mixed solution from the first diluting chamber 43 to the stirring chamber 46 is performed while the high concentration reagent and the RO water are being supplied to the second diluting chamber 44 by the diaphragm pumps 45*a* and 45*b*. Thereafter, the supplying operation of the high concentration reagent and the RO water to the second diluting chamber 44 is completed at timing t7, and the liquid level of the mixed solution in the second diluting chamber 44 becomes full (about 300 mL). When the reagent in the first diluting chamber 43 becomes empty, the termination of the supply of reagent to the stirring chamber 46 is detected at timing t7 when the float switch 103 reaches the lower limit (L).

At timing t7 when the first diluting chamber 43 becomes empty, the supplying operation of the high concentration reagent and the RO water to the first diluting chamber 43 by the diaphragm pumps 45*a* and 45*b* ("supply by DP" between timing t7 to t9) starts (step S17 of FIG. 16 starts). The liquid level of the first diluting chamber 43 rises from timing t7. At timing t7, the supply of reagent from the stirring chamber 46 to the supply chamber 47 starts when the reagent in the supply chamber 47 again reduces to about half the amount (about 300 mL) and the float switch 106 reaches the lower limit position (L). The liquid level of the supply chamber 47 then rises and the liquid level of the stirring chamber 46 lowers from timing t7.

Thereafter, the operations after timing t8 are performed by repeating the operations between timing t4 and t8 until the measurement by the measurement section 2 is terminated. Thus, the dilution of the high concentration reagent (supply of two liquids, RO water and high concentration reagent) are continuously carried without being interrupted by alternately performing the supplying operation of the high concentration reagent and the RO water to the first diluting chamber 43 (timing t3 to t5, timing t7 to t9), and the supplying operation of the high concentration reagent and the RO water to the second diluting chamber 44 (timing t5 to t7). That is, in the first embodiment, the supplying operation of the high concentration reagent and the RO water to the two diluting chambers (first diluting chamber 43 and second diluting chamber 44) and the supplying operation of the mixed solution from the two diluting chambers (first diluting chamber 43 and second diluting chamber 44) to the stirring chamber 46 are alternately performed, and the respective supplying operation can be performed in parallel to each other (intervals I1 and I2), and hence the supply of the high concentration reagent and the RO water can be continuously performed without being interrupted.

In the first embodiment, predetermined electromagnetic valve 217 and the like are opened to supply the negative pressure force from the negative pressure source 61 while the diaphragm pumps 45a and 45b are performing the supplying operation of the high concentration reagent and the RO water to the first diluting chamber 43, so that the operation of each unit is controlled such that the supplying operation of the mixed solution accommodated in the second diluting chamber 44 to the stirring chamber 46 can be performed, and furthermore, the supplying operation of the mixed solution from the second diluting chamber 44 to the stirring chamber 46 is performed in parallel (interval I1) even while performing the supplying operation of the high concentration reagent and the RO water to the first diluting chamber 43, and hence the accommodation of the mixed solution (preparation of reagent) can start in the first diluting chamber 43 without waiting for the total amount of mixed solution accommodated in the second diluting chamber 44 from being supplied to the stirring chamber 46. That is, the mixed solution can be accommodated in the first diluting chamber 43 at the time point the total amount of mixed solution of the second diluting chamber 44 is supplied to the stirring chamber 46. Thus, the preparing amount of the reagent (mixed solution) can be increased compared to the prior art by the amount of mixed solution accommodated in the first diluting chamber 43 while the mixed solution of the second diluting chamber 44 is being supplied to the stirring chamber 46.

In the first embodiment, control is made such that the supplying operation of the mixed solution accommodated in the first diluting chamber 43 to the stirring chamber 46 is performed (interval I2) while performing the supplying operation of the high concentration reagent and the RO water to the second diluting chamber 44 by the CPU 49a, so that the reagent (mixed solution) can be prepared in the first diluting chamber 43 while the prepared reagent (mixed solution) is being supplied from the second diluting chamber 44 to the stirring chamber 46, and furthermore, the reagent (mixed solution) can be prepared (interval I2) in the second diluting chamber 44 while the prepared reagent (mixed solution) is being supplied from the first diluting chamber 43 to the stirring chamber 46. The amount of reagent prepared within a predetermined time then can be further increased.

In the first embodiment, control is performed such that the supplying operation of the high concentration reagent and the RO water to the first diluting chamber 43 and the supplying operation of the high concentration reagent and the RO water to the second diluting chamber 44 are alternately executed by the CPU 49a, so that the supplying operation of the high concentration reagent and the RO water to the first diluting chamber 43 or the second diluting chamber 44 can be continuously performed without being interrupted while supplying the mixed solution to the stirring chamber 46.

In the first embodiment, a bent pipe 461 is arranged in the stirring chamber 46 and the mixed solution is stirred by being supplied to the stirring chamber 46, and thus the device configuration can be simplified compared to when separately arranging the motor and the propeller for stirring in the stirring chamber 46.

In the first embodiment, the supply chamber 47 can accommodate a total amount (about 600 mL) of reagent of the maximum liquid amount (about 300 mL) of the mixed solution accommodated in the first diluting chamber 43 and the maximum liquid amount (about 300 mL) of the mixed solution accommodated in the second diluting chamber 44, so that the total amount of mixed solution accommodated in the first diluting chamber 43 or the second diluting chamber 44 can be supplied all at once at the time point the reagent accommodated in the supply chamber 47 is supplied to the measurement section 2 by the total amount (maximum liquid amount of about 300 mL) of the mixed solution accommodated in the first diluting chamber 43 (second diluting chamber 44). Thus, the supplying operation of the mixed solution can be simplified compared to when supplying the mixed solution from the first diluting chamber 43 (second diluting chamber 44) to the stirring chamber 46 over plural times.

In the first embodiment, the first diluting chamber 43 and the second diluting chamber 44 are configured to have substantially the same capacity (e.g., about 350 mL), hence, the supplying amount of the high concentration reagent and the supplying amount of the RO water supplied to the first diluting chamber 43 and the second diluting chamber 44 may be made the same for the first diluting chamber 43 and the second diluting chamber 44 to have the mixed solution at the desired concentration. Thus, the supplying operation of the high concentration reagent and the RO water can be simplified since the supplying amount of the high concentration reagent and the RO water does not need to be changed depending on the supplying destination (first diluting chamber 43 or second diluting chamber 44) of the high concentration reagent and the RO water to obtain the reagent of predetermined concentration.

Second Embodiment

A second embodiment will be described with reference to FIGS. 20 and 21. In the second embodiment, a reagent preparing device 600 in which the RO water producing unit 700 is arranged at the exterior is used as part of the blood analyzer 800, different from the first embodiment, will be described.

Figure 20:
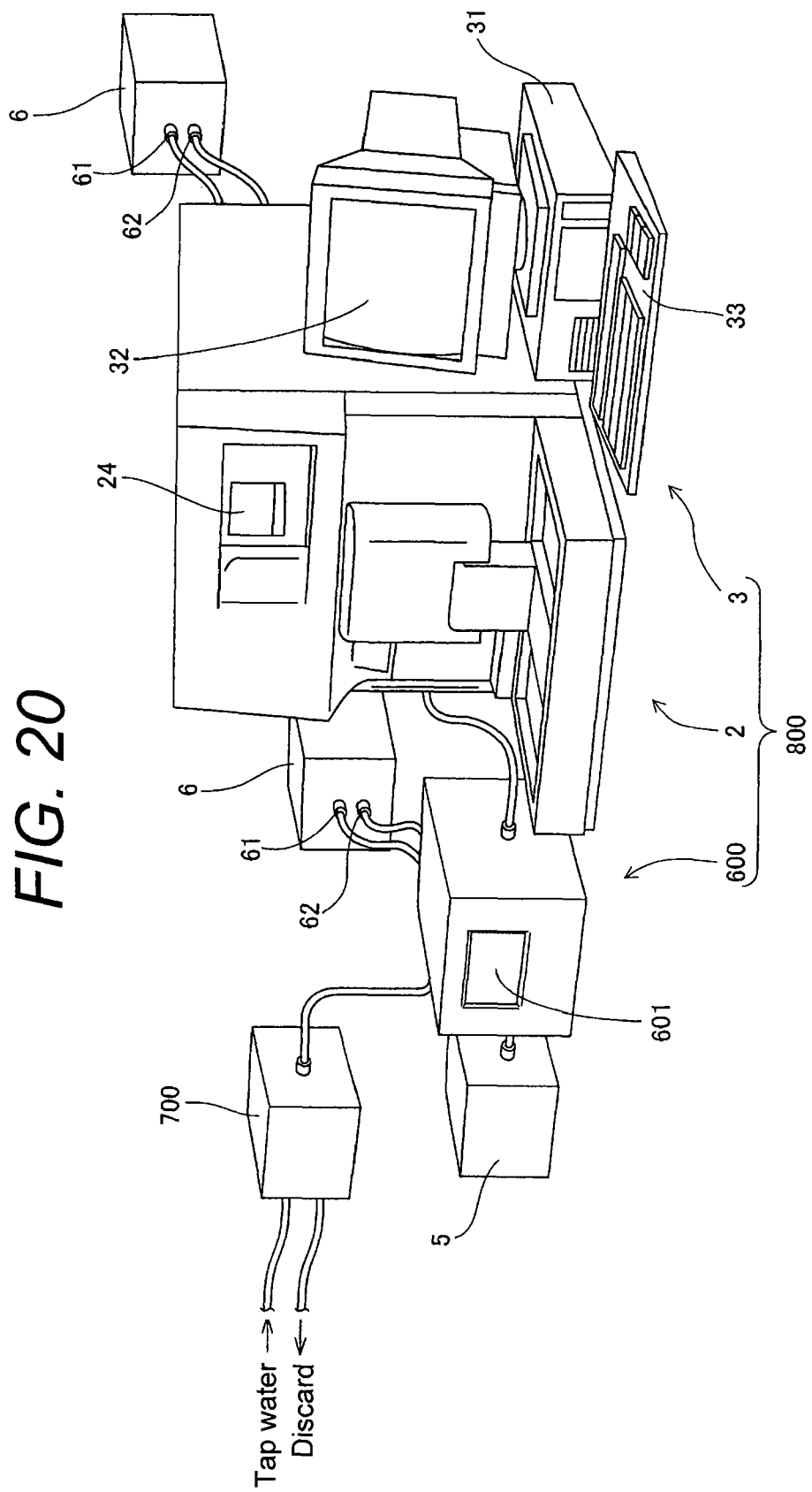
FIG. 20 is a perspective view showing a blood analyzer including the reagent preparing device according to a second embodiment of the present invention.

As shown in FIG. 20, the blood analyzer 800 is configured by the measurement section 2 having a function of measuring blood, the data processing section 3 for analyzing the measurement data output from the measurement section 2 and obtaining an analysis result, and the reagent preparing device 600 for preparing a reagent to be used in the processing of specimens.

Figure 21:
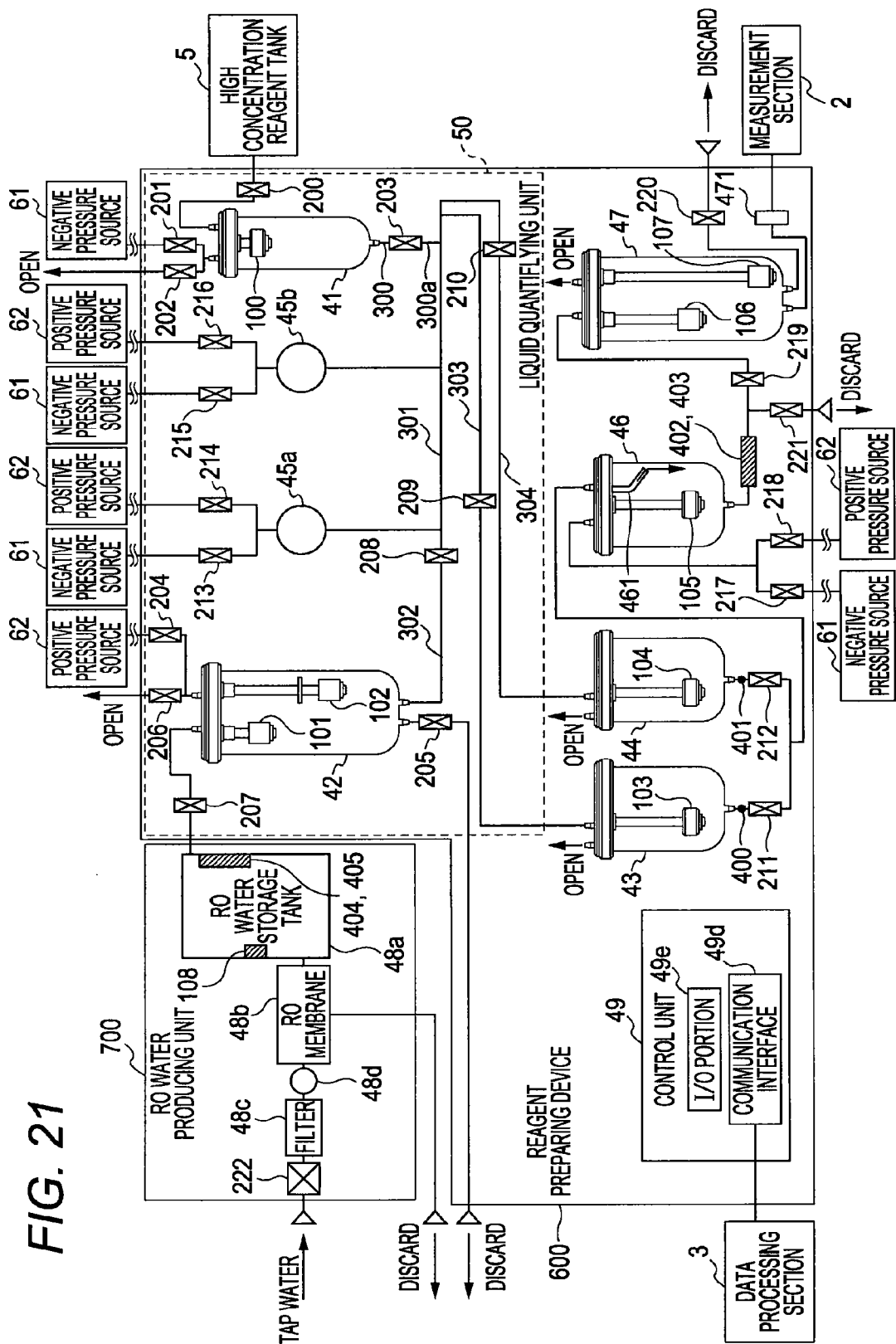
FIG. 21 is a block diagram showing a configuration of the reagent preparing device according to the second embodiment shown in FIG. 20.

As shown in FIGS. 20 and 21, in the second embodiment, the reagent preparing device 600 is configured to prepare the reagent to be used in blood analysis by diluting the high concentration reagent to a desired concentration using the RO water produced by the RO water producing unit 700 arranged at the exterior.

As shown in FIG. 20, the reagent preparing device 600 includes a touch panel type display unit 601. The CPU 49a of the reagent preparing device 600 is configured to accept instructions such as activation of the reagent preparing device 600, shutdown, and various types of settings from the user through the touch panel type display unit 601.

Other structures of the second embodiment are similar to those of the first embodiment.

In the second embodiment, the configuration of the reagent preparing device 600 is simplified by arranging the RO water producing unit 700 at the exterior of the reagent preparing device 600.

Other effects of the second embodiment are similar to the first embodiment.

The embodiments disclosed herein are illustrative in all aspects and should not be construed as being exclusive. The scope of the invention is defined by the Claims rather than by the description of the embodiments made above, and all modifications equivalent in meaning to the Claims and within the scope of the Claims are to be encompassed.

For instance, an example of diluting the high concentration reagent to 25 times has been described in the first embodiment and the second embodiment, but the present invention is not limited thereto, and the high concentration reagent may be diluted to magnifications other than 25 times such as 20 times. In this case, after quantifying the RO water once using the diaphragm pumps 45a and 45b, the high concentration reagent is quantified once, and then the RO water is quantified 18 times to prepare the reagent having a diluting magnification of 20 times.

In the first embodiment and the second embodiment, an example in which after the RO water serving as the diluting liquid is quantified once, the high concentration reagent is quantified once, and then the RO water is quantified 23 times to prepare the reagent having a diluting magnification of 25 times has been described, but the present invention is not limited thereto, and after the RO water is quantified twice, the high concentration reagent may be quantified once and then the RO water may be quantified 22 times to prepare a reagent having a diluting magnification of 25 times.

In the first embodiment and the second embodiment, an example in which two diaphragm pumps 45a and 45b are arranged has been described, but the present invention is not limited thereto, and one diaphragm pump may be arranged, or three or more diaphragm pumps may be arranged.

Furthermore, in the first embodiment and the second embodiment, an example in which the diaphragm pump is commonly used both to supply the RO water and to supply the high concentration reagent has been described, but the present invention is not limited thereto, and a plurality of diaphragm pumps may be arranged, and the supply of the RO water and the supply of the high concentration reagent may be carried out using different diaphragm pumps.

In the first embodiment and the second embodiment, an example of quantifying the RO water and the high concentration reagent using the diaphragm pump has been described, but the present invention is not limited thereto, and the RO water and the high concentration reagent may be quantified using a syringe pump in which the amount of stroke of the piston is fixed as long as it is a quantifier that can quantify a constant amount of liquid defined in advance in one quantifying operation.

Figure 22:
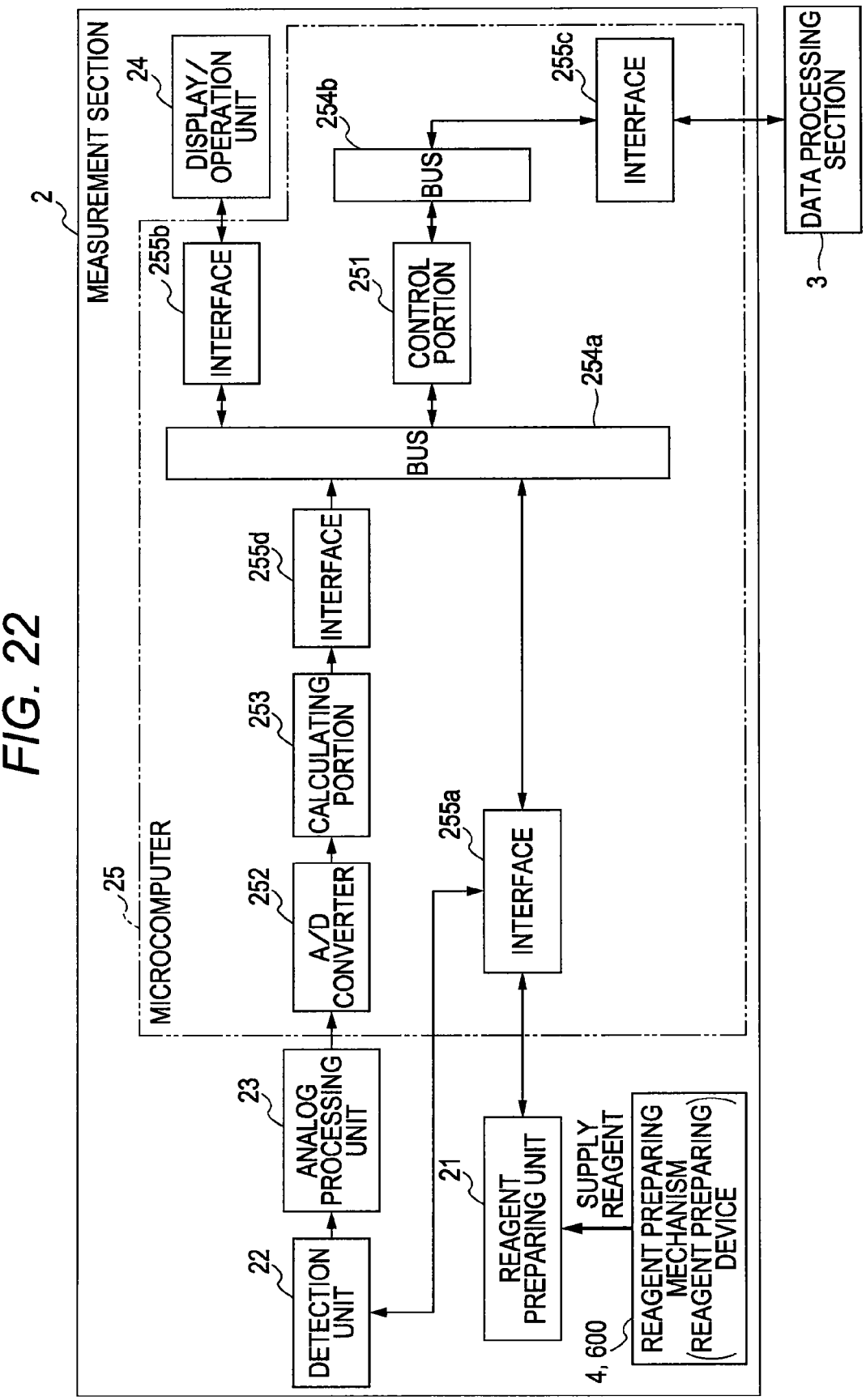
FIG. 22 is a block diagram describing a variant of the reagent preparing device according to the first embodiment shown in FIG. 1 and the second embodiment shown in FIG. 20.

In the first embodiment and the second embodiment, the reagent preparing device installed separate from the measurement section has been described as one example of the reagent preparing device, but the present invention is not limited thereto, and it may be a reagent preparing device arranged in the measurement section and having a function of a reagent preparing mechanism, as shown in a variant of FIG. 22. The measurement section (device) equipped with the reagent preparing mechanism includes blood cell counting device, immune measurement device, and smear producing device, and is particularly suited to the blood cell counting device in which the usage amount of the diluting liquid is large.

Similarly, in the first embodiment and the second embodiment, a blood analyzer separately including the measurement section and the reagent preparing device has been shown as an example of a specimen processing system, but the present invention is not limited thereto, and may be a blood analyzer including the measurement section and the reagent preparing mechanism arranged in the measurement section. In the blood analyzer, each chamber of the reagent preparing device may not be arranged in a single device, and the stirring chamber and two diluting chambers may be arranged on the device for preparing the reagent, and the supply chamber for waiting the reagent to use for the measurement may be arranged on the device on the measurement section side. Both the stirring chamber and the supply chamber may be arranged in the device on the measurement section side. Both the stirring chamber and the supply chamber may be omitted, and the measurement section may directly aspirate the mixed solution from the diluting chamber. The high concentration reagent chamber may be omitted to supply the high concentration reagent from the high concentration reagent tank to the diluting chamber, and the RO water chamber may be omitted to supply the pure water from the pure water purifying device arranged at the exterior of the reagent preparing device to the diluting chamber.

In the first embodiment, an example in which the pneumatic unit 7 is arranged in the measurement section 2 and the measurement section aspirates the reagent from the supply chamber 47 of the reagent supply device 4 has been described, but the present invention is not limited thereto, and the pneumatic unit for aspirating the reagent to the measurement section side may not be arranged and the supply (flow) of reagent from the reagent preparing device side to the measurement section may be carried out using the pneumatic unit (positive pressure source) of the reagent preparing device.

In the first embodiment and the second embodiment, the mixed solution is stirred in the stirring chamber, but the present invention is not limited thereto, the mixed solution may be stirred in the first diluting chamber (second diluting chamber).

In the first embodiment and the second embodiment, the bent pipe is arranged in the stirring chamber, and the mixed solution is stirred by flowing the mixed solution transferred from the first diluting chamber (second diluting chamber) along the inner wall surface of the stirring chamber, but the present invention is not limited thereto, and the mixed solution may be stirred by structures other than the bent pipe.

In the first embodiment and the second embodiment, the mixed solution is supplied from the first diluting chamber and the second diluting chamber to one stirring chamber, but the present invention is not limited thereto, and two stirring chambers corresponding to the first diluting chamber and the second diluting chamber, respectively, may be arranged.

In the first embodiment and the second embodiment, the reagent preparing device includes the stirring chamber for stirring the mixed solution supplied from the first diluting chamber (second diluting chamber), and the supply chamber for accommodating the reagent waiting to be supplied to the measurement section, but the present invention is not limited thereto, and one of the stirring chamber or the supply chamber may be omitted, and one chamber having both functions of stirring the mixed solution and waiting to supply the regent may be arranged.

In the first embodiment and the second embodiment, the reagent preparing device includes two diluting chambers, but the present invention is not limited thereto, and may include three or more diluting chambers.

In the first embodiment and the second embodiment, the supplying operation of supplying the mixed solution in the second diluting chamber to the stirring chamber is performed while the reagent preparing device is performing the supplying operation of supplying the high concentration reagent and the RO water to the first diluting chamber, and the supplying operation of supplying the mixed solution in the first diluting chamber to the stirring chamber is performed while the reagent preparing device is performing the supplying operation of supplying the high concentration reagent and the RO water to the second diluting chamber. However, the present invention is not limited thereto, and the supplying operation of supplying the mixed solution in the second diluting chamber to the stirring chamber may be performed while the reagent preparing device is performing the supplying operation of supplying the high concentration reagent and the RO water to the first diluting chamber, but the supplying operation of supplying the mixed solution in the first diluting chamber to the stirring chamber may not be performed while the reagent preparing device is performing the supplying operation of supplying the high concentration reagent and the RO water to the second diluting chamber.

What is claimed is:

1. A reagent preparing device configured to supply a mixed solution, which is a mixture of water and concentrated reagent containing an antiseptic agent, to a measurement section that uses the mixed solution as a reagent to analyze a specimen, the reagent preparing device comprising:
a supply chamber in which the mixed solution of a desired concentration is storable for stable supply of the mixed solution to the measurement section;
a first diluting chamber configured to perform a diluting process in which the concentrated reagent is diluted with the water to prepare the mixed solution of the desired concentration, the first diluting chamber being communicable, by operation of a first valve set, with the supply chamber via a mixed solution path to supply the mixed solution from the first diluting chamber to the supply chamber;
a second diluting chamber configured to perform the diluting process, the second diluting chamber being communicable, by operation of a second valve set, with the supply chamber via the mixed solution path to supply the mixed solution From the second diluting chamber to the supply chamber;
a water chamber in which the water is storable, the water chamber being communicable, by operation of a water valve set, with the first and second diluting chambers via a water/reagent path to supply the water to the first and second diluting chambers, the water chamber being equipped with a drain valve for draining the water from the water chamber;
a concentrated reagent chamber in which the concentrated reagent is storable, the concentrated reagent chamber being communicable, by operation of a reagent valve set, with the first and second diluent chambers via the water/reagent path to supply the concentrated reagent to the first and second diluting chambers; and
a controller programmed to operate the water valve set to supply the water from the water chamber selectively to the first or second diluting chamber via the water/reagent path, and operate the reagent valve set to supply the concentrated reagent from the concentrated reagent chamber selectively to the first or second diluting chamber via the water/reagent path,
wherein the controller is further programmed to perform, when the controller receives a shutdown instruction, operations which include:
(a) when the controller receives the shutdown instruction, if the diluting process is in progress in one of the first diluting chamber and the second diluting chamber, operate the water valve set and the reagent valve set to continue supply of the water and the concentrated reagent via the water/reagent path from the water chamber and the concentrated reagent chamber to the one diluting chamber until the one diluting chamber receives sufficient supply of the water and the concentrated reagent to prepare the mixed solution of the desired concentration;
(b) after the one diluting chamber receives sufficient supply of the water and the concentrated reagent to prepare the mixed solution of the desired solution, operate the drain valve to discard the water from the water chamber without discarding the mixed solution reagent in the supply chamber;
(c) after the water is discarded from the water chamber, terminate operation of the reagent preparing device according to the received shutdown instruction; and
(d) when the controller receives the shutdown instruction, if the supply chamber stores sufficient supply of the mixed solution of the desired concentration, and the diluting process is in progress in neither the first nor second diluting chamber, operate the drain valve to discard the water from the water chamber without discarding the mixed solution in the supply chamber and terminate operation of the reagent preparing device according to the received shutdown instruction.

2. The reagent preparing device according to claim 1, further comprising a stirring chamber in which the mixed solution is stirred, the stirring chamber being located in the mixed solution path and communicable with the first and second diluting chambers and the supply chamber, wherein the controller is programmed to operate the second valve set to supply the mixed solution from the second diluting chamber to the stirring chamber when a predetermined amount of the mixed solution is stored in the second diluting chamber.

3. The reagent preparing device according to claim 2, wherein the controller is programmed to operate the water valve set and the reagent valve sets to supply the water and the concentrated reagent to the first diluting chamber while the controller controls the operates the second valve sets to supply the mixed solution from the second diluting chamber to the stirring chamber.

4. The reagent preparing device according to claim 3, wherein after a predetermined amount of the mixed solution is stored in the first diluting chamber, and an insufficient amount of the mixed solution is stored in the second diluting chamber, the controller is programmed to operate the first valve set to supply the mixed solution from the first diluting chamber to the stirring chamber while the controller operate the water valve set and the reagent valve set to supply the water and the concentrated reagent to the second diluting chamber.

5. The reagent preparing device according to claim 2, wherein the stirring chamber is supplied with the mixed solution from at least one of the first diluting chamber and the second diluting chamber.

6. The reagent preparing device according to claim 5, wherein the stirring chamber is configured to stir the supplied mixed solution when the stirring chamber is supplied with the mixed solution is supplied.

7. The reagent preparing device according to claim 6, wherein the supply chamber is configured to store the mixed solution of an amount greater than or equal to a total amount of the mixed solution storable in in the first and second diluting chambers.

8. The reagent preparing device according to claim 1, wherein the controller is programmed to operate the water valve set and the reagent valve set to supply, from the water chamber and the concentrated reagent chamber, the water and the concentrated reagent selectively to only one of the first and second diluting chambers at a time.

9. The reagent preparing device according to claim 1, wherein the controller is programmed to selectively operate the water valve set and the reagent valve set to alternately supply the water and the concentrated reagent from the water chamber and the concentrated reagent to the first and second diluting chambers.

10. The reagent preparing device according to claim 1, wherein the first diluting chamber and the second diluting chamber are substantially equal in capacity.

11. The reagent preparing device according to claim 1, further comprising:
a pneumatic pressure system operable to generate positive and negative pressures for use in transferring the water and the concentrated reagent; and
pressure valves operable to switch supply of the positive and negative pressures generated by the pneumatic pressure system,
wherein the controller is programmed to operate the pressure valves to alternately supply the positive and negative pressures to transfer the water and the concentrated reagent.

12. The reagent preparing device according to claim 11, further comprising:
a first pump operated by the positive and negative pressures from the pneumatic pressure system to repeat a draw and a discharge of a quantified amount of the water or the concentrated reagent to supply the water or the concentrated reagent to the first diluting chamber; and
a second pump operated by the positive and negative pressures from the pneumatic pressure system to repeat a draw and a discharge of the qualified amount of the water or the concentrated reagent to supply the water and the concentrated reagent to the first diluting chamber.

13. The reagent preparing device according to claim 12, wherein the controller is programmed to operate the pressure valves to simultaneously operate the first and second pumps while supplying the water and the concentrated reagent to the first diluting chamber.

14. The reagent preparing device according to claim 12, wherein
the first pump is further operated by the positive and negative pressures from the pneumatic pressure system to supply the water and the concentrated reagent to the second diluting chambers; and the second pump is further operated by the positive and negative pressures from the pneumatic pressure system to supply the water and the concentrated reagent to the second diluting chamber.

15. The reagent preparing device according to claim 1, wherein, when the shutdown instruction is received, the controller is programmed to:
determine whether insufficient supply of the mixed solution is left in the supply chamber, and the diluting process is in progress in one of the first and second diluting chambers to make up for the insufficient supply of the mixed solution left in the supply chamber; and
responsive to a determination that insufficient supply of the mixed solution is left in the supply chamber, and the diluting process is in progress in the one diluting chamber to make up for the insufficient supply of the mixed solution left in the supply chamber, operate the water valve set and the reagent valve set to continue supply of the water and the concentrated reagent, after the controller receives the shutdown instruction, via the water/reagent path from the water chamber and the concentrated reagent chamber to the one diluting chamber until the one diluting chamber receives sufficient supply of the water and the concentrated reagent to prepare the mixed solution of the desired concentration.

16. The reagent preparing device according to claim 1, wherein, when the shutdown instruction is received, the controller is programmed to:
determine whether insufficient supply of the mixed solution is left in the supply chamber, and the diluting process is in progress in one of the first and second diluting chambers to make up for the insufficient supply of the mixed solution left in the supply chamber; and
responsive to a determination that the supply chamber stores sufficient supply of the mixed solution of the desired concentration, and the mixing process is in progress in neither the first nor second diluting chamber, operate the drain valve to discard the water from the water chamber immediately.

17. A specimen processing system comprising:
a measurement section configured to analyze a specimen using a mixed solution as a reagent which is a mixture of water and concentrated reagent containing an antiseptic agent;
a supply chamber in which the mixed solution of a desired concentration is storable for stable supply of the mixed solution to the measurement section;
a first diluting chamber configured to perform a diluting process in which the concentrated reagent is diluted with the water to prepare the mixed solution of the desired concentration, the first diluting chamber being communicative, by operation of a first valve set, with the supply chamber via a mixed solution path to supply the mixed solution from the first diluting chamber to the supply chamber;
a second diluting chamber configured to perform the diluting process, the second diluting chamber being communicative, by operation of a second valve set, with the supply chamber via the mixed solution path to supply the mixed solution from the second diluting chamber to the supply chamber;
a water chamber in which the water is storable, the water chamber being communicative, by operation of a water valve set, with the first and second diluting chambers via a water/reagent path to supply the water to the first and second diluting chambers, the water chamber being equipped with a drain valve for draining the water from the water chamber;

a concentrated reagent chamber in which the concentrated reagent is storable, the concentrated reagent chamber being communicable, by operation of a reagent valve set, with the first and second diluting chambers via the water/reagent path to supply the concentrated reagent to the first and second diluting chambers; and a controller programmed to operate the water valve set to supply the water from the water chamber selectively to the first or second diluting chamber via the water/reagent path, and operate the reagent valve set to supply the concentrated reagent from the concentrated reagent chamber selectively to the first or second diluting chamber via the water/reagent path, wherein the controller is further programmed to perform the following operations when the controller receives a shutdown instruction, the operations including:

(a) when the controller receives the shutdown instruction if the diluting process is in progress in one of the first and second diluting chambers, operate the water valve set and the reagent valve set to continue supply of the water and the concentrated reagent via the water/reagent path from the water chamber and the concentrated reagent chamber to the one diluting chamber until the one diluting chamber receives sufficient supply of the water and the concentrated reagent to prepare the mixed solution of the desired concentration;

(b) after the one diluting chamber receives sufficient supply of the water and the concentrated reagent to prepare the mixed solution of the desired concentration, operate drain valve to discard the water from the water chamber without discarding the mixed solution in the supply chamber;

(c) after the water is discarded from the water chamber, terminate operation of the reagent preparing device according to the received shutdown instruction; and (d) when the controller receives the shutdown instruction, if the supply chamber stores sufficient supply of the mixed solution of the desired concentration, and the mixing process is in progress in neither the first nor second diluting chamber, operate the drain valve to discard the water from the water chamber without discarding the mixed solution in the supply chamber and terminate operation of the reagent preparing device according to the received shutdown instruction.

18. The specimen processing system according to claim 17, further comprising:

a stirring chamber in which the mixed solution is stirred, the stirring chamber being located in the mixed reagent path and communicable with the first and second diluting chambers and the supply chamber, wherein the controller is programmed to operate at least one of the first and second valve sets to supply the mixed solution to the stirring chamber from at least one of the first and second diluting chambers, and an aspirator provided in the measurement section, the aspirator being operable to aspire the mixed solution sent from the supply chamber.

19. A reagent preparing method for preparing a mixed solution, which is a mixture of water and concentrated reagent containing an antiseptic agent, and supplying the mixed solution as a reagent to a measurement section that uses the mixed solution to analyze a specimen, the reagent preparing method comprising:

(a) storing the water in a water chamber and storing the concentrated reagent in a concentrated reagent chamber;

(b) supplying the water from the water chamber and the concentrated reagent from the concentrated reagent chamber to a first diluting chamber which performs a diluting process in which the supplied concentrated reagent is diluted with the supplied water to prepare the mixed solution of a desired concentration; and (c) supplying the water from the water chamber and the concentrated reagent from the concentrated reagent chamber to a second diluting chamber which performs the diluting process;

(d) supplying the mixed solution from one of the first dilution chamber and the second dilution chamber to a supply chamber, which stores the mixed solution of the desired concentration for stable supply of the mixed solution to be supplied to the measurement section;

(e) responsive to receipt of a shutdown instruction, if the diluting process is in progress in one of the first and second diluting chambers, performing Step (b) or (c) to continue supplying the water and the concentrated reagent to the one diluting chamber after reception of the shutdown instruction until the one diluting chamber receives sufficient supply of the water and the concentrated reagent to prepare the mixed solution of the desired concentration, (f) after the one diluting chamber receives sufficient supply of the water and the concentrated reagent to prepare the mixed solution of the desired concentration, discarding the water from the water chamber without discarding the mixed solution in the supply chamber and:

(g) after the water is discarded from the water chamber, terminating operation of the reagent preparing device according to the received shutdown instruction; and (h) responsive to receipt of the shutdown instruction, if the supply chamber stores sufficient supply of the mixed solution of the desired concentration, and the diluting process is in progress in neither the first nor second diluting chamber, discarding the water from the water chamber without discarding the mixed solution in the supply chamber and terminating operation of the reagent preparing device according to the received shutdown instruction, wherein Steps (b) and (c) are alternately executed.

20. The reagent preparing method according to claim 19, wherein Step (d) comprises:

(d1) supplying the mixed solution from the first diluting chamber to the supply chamber via a stirring chamber located between the first diluting chamber and the supply chamber; and (d2) supplying the mixed solution from the second diluting chamber to the supply chamber via the stirring chamber, wherein Steps (d1) and (d2) are alternately executed.

21. The reagent preparing method according to claim 20, wherein Steps (b) and (d2) are executed in parallel, and Steps (c) and (d1) are executed in parallel.

* * * * *

UNITED STATES PATENT AND TRADEMARK OFFICE
CERTIFICATE OF CORRECTION

PATENT NO. : 9,164,021 B2  
APPLICATION NO. : 12/711676  
DATED : October 20, 2015  
INVENTOR(S) : Koichi Okubo et al.

Page 1 of 1

It is certified that error appears in the above-identified patent and that said Letters Patent is hereby corrected as shown below:

In the Claims

In column 27, claim 1, line 62, after "mixed solution" replace "From" with --from--.

In column 28, claim 1, line 34, after "the mixed solution" delete "reagent".

In column 28, claim 3, line 59, before "operates the second valve" delete "controls the".

In column 29, claim 6, line 12, after "mixed" replace "solution is supplied." with --solution.--.

In column 29, claim 14, line 67, after "second diluting" replace "chambers;" with --chamber;--.

In column 32, claim 19, line 20, after "the mixed solution" delete "to be supplied".

In column 32, claim 19, line 34, after "the supply chamber" replace "and:" with --and;--.

Signed and Sealed this  
Twenty-ninth Day of March, 2016

Michelle K. Lee  
*Director of the United States Patent and Trademark Office*